United States Patent
Lim et al.

(10) Patent No.: US 7,863,140 B2
(45) Date of Patent: Jan. 4, 2011

(54) METHODS OF MAKING A MOLECULAR DETECTION CHIP HAVING A METAL OXIDE SILICON FIELD EFFECT TRANSISTOR ON SIDEWALLS OF A MICRO-FLUID CHANNEL

(75) Inventors: Geun-Bae Lim, Gyeonggi-do (KR); Chin-Sung Park, Gyeonggi-do (KR); Yoon-Kyoung Cho, Gyeonggi-do (KR); Sun-Hee Kim, Gyeonggi-do (KR)

(73) Assignee: Samsung Electronics Co., Ltd. (KR)

(*) Notice: Subject to any disclaimer, the term of this patent is extended or adjusted under 35 U.S.C. 154(b) by 5 days.

(21) Appl. No.: 11/755,952

(22) Filed: May 31, 2007

(65) Prior Publication Data
US 2007/0218610 A1    Sep. 20, 2007

Related U.S. Application Data

(62) Division of application No. 10/239,736, filed as application No. PCT/KR02/00746 on Apr. 23, 2002, now Pat. No. 7,235,389.

(30) Foreign Application Priority Data

| Apr. 23, 2001 | (KR) | ............... 2001-21752 |
| May 29, 2001 | (KR) | ............... 2001-29729 |
| Dec. 11, 2001 | (KR) | ............... 2001-78010 |

(51) Int. Cl.
*H01L 21/336* (2006.01)
*G01N 27/02* (2006.01)
*C12M 1/34* (2006.01)

(52) U.S. Cl. ............ 438/280; 435/174; 435/283.1; 435/287.2; 422/68.1; 422/82.01; 257/E21.051; 438/289

(58) Field of Classification Search ............ 438/280
See application file for complete search history.

(56) References Cited

U.S. PATENT DOCUMENTS

| 4,238,757 A | 12/1980 | Schenck |
| 4,325,181 A * | 4/1982 | Yoder ............ 438/180 |
| 4,460,910 A * | 7/1984 | Chappell et al. ............ 257/192 |

(Continued)

FOREIGN PATENT DOCUMENTS

CN      1205079 A      1/1999

(Continued)

OTHER PUBLICATIONS

Böhm et al. "A flow-through cell with integrated coulometric pH actuator" *Sensors and Actuators B*, 47(1-3):48-53 (1998).

(Continued)

*Primary Examiner*—Charles D Garber
*Assistant Examiner*—Pape Sene
(74) *Attorney, Agent, or Firm*—Myers Bigel Sibley & Sajovec, PA

(57) ABSTRACT

A molecular detection chip including a metal oxide silicon-field effect transistor (MOSFET) on sidewalls of a micro-fluid channel and a molecular detection device including the molecular detection chip are provided. A molecular detection method, particularly, qualification methods for the immobilization of molecular probes and the binding of a target sample to the molecular probes, using the molecular detection device, and a nucleic acid mutation assay device and method are also provided. The formation of the MOSFET on the sidewalls of the micro-fluid channel makes easier to highly integrate a molecular detection chip. In addition, immobilization of probes directly on the surface of a gate electrode ensures the molecular detection chip to check for the immobilization of probes and coupling of a target molecule to the probes in situ.

10 Claims, 13 Drawing Sheets

U.S. PATENT DOCUMENTS

| | | | |
|---|---|---|---|
| 4,478,222 A | | 10/1984 | Koning et al. |
| 4,657,658 A | | 4/1987 | Sibbald |
| 4,764,797 A | | 8/1988 | Shaw et al. |
| 4,777,019 A | | 10/1988 | Dandekar |
| 4,874,499 A | | 10/1989 | Smith et al. |
| 4,877,582 A | | 10/1989 | Oda et al. |
| 5,078,855 A | * | 1/1992 | Mochizuki et al. .......... 204/418 |
| 5,272,913 A | * | 12/1993 | Toda et al. .................... 73/105 |
| 5,396,089 A | * | 3/1995 | Wieck et al. ................ 257/192 |
| 5,466,348 A | * | 11/1995 | Holm-Kennedy ........... 205/775 |
| 5,589,688 A | * | 12/1996 | Kimura et al. ............ 250/338.4 |
| 5,662,768 A | * | 9/1997 | Rostoker .................... 257/301 |
| 5,701,017 A | * | 12/1997 | Patel et al. .................... 257/27 |
| 5,827,482 A | | 10/1998 | Shieh et al. |
| 5,892,252 A | | 4/1999 | Hammond et al. |
| 5,995,209 A | | 11/1999 | Ohman et al. |
| 6,060,327 A | | 5/2000 | Keen |
| 6,085,576 A | | 7/2000 | Sunshine et al. |
| 6,093,612 A | | 7/2000 | Suh |
| 6,144,447 A | | 11/2000 | Ohman et al. |
| 6,171,850 B1 | | 1/2001 | Nagle et al. |
| 6,212,956 B1 | * | 4/2001 | Donald et al. ................. 73/724 |
| 6,287,776 B1 | | 9/2001 | Hefti |
| 6,482,639 B2 | | 11/2002 | Snow et al. |
| 6,534,379 B1 | * | 3/2003 | Fisher et al. ................ 438/424 |
| 6,537,437 B1 | * | 3/2003 | Galambos et al. ........... 204/600 |
| 6,766,817 B2 | | 7/2004 | da Silva |
| 6,918,404 B2 | | 7/2005 | da Silva |
| 7,066,586 B2 | | 6/2006 | da Silva |
| 7,781,167 B2 | * | 8/2010 | Lim et al. ....................... 435/6 |
| 2002/0127736 A1 | * | 9/2002 | Chou et al. .................. 436/180 |
| 2002/0177135 A1 | | 11/2002 | Doung et al. |
| 2003/0036054 A1 | * | 2/2003 | Ladisch et al. .................. 435/5 |
| 2005/0170347 A1 | * | 8/2005 | Miyahara et al. ................ 435/6 |

FOREIGN PATENT DOCUMENTS

| | | |
|---|---|---|
| DE | 44 42 685 C1 | 3/1996 |
| EP | 0 633 468 A2 | 1/1995 |
| EP | 0 740 151 A1 | 10/1996 |
| GB | 2 236 903 A | 4/1991 |
| JP | 53-146693 | 12/1978 |
| JP | 58-184540 A | 10/1983 |
| JP | 59-178353 A | 10/1984 |
| JP | 62-263460 A | 11/1987 |
| JP | 1-107144 A | 4/1989 |
| JP | 10-80266 A | 3/1998 |
| JP | 11-505606 A | 5/1999 |
| NL | 8602669 A | 5/1988 |
| WO | WO 93/08464 A1 | 4/1993 |
| WO | WO 99/41606 A1 | 8/1999 |
| WO | WO 99/44046 A1 | 9/1999 |
| WO | WO 99/50643 A1 | 10/1999 |
| WO | WO 00/75276 A2 | 12/2000 |
| WO | WO 01/13432 A1 | 2/2001 |

OTHER PUBLICATIONS

International Search Report, PCT/KR02/00746, Apr. 23, 2002.

Lauwers et al. "A CMOS Multi-Parameter Biochemical Microsensor with Temperature Control and Signal Interfacing" *Digest of Technical Papers—2001 IEEE International Solid-State Circuits Conference*, pp. 244-245+452 (2001).

Perkins et al. "An Active Microelectronic Transducer for Enabling Label-Free Miniaturized Chemical Sensors" *Technical Digest—2000 IEDM International Electron Devices Meeting*, pp. 407-410 (2000).

Sakurai et al. "Real-Time Monitoring of DNA Polymerase Reactions by a Micro ISFET pH Sensor" *Anal. Chem.* 64:1996-1997 (1992).

Supplementary European Search Report, EP 02 72 0663, Nov. 2, 2006.

Tsuruta et al. "Detection of the products of polymerase chain reaction by an ELISA system based on an ion sensitive field effect transistor" *Journal of Immunological Methods* 176:45-52 (1994.

Tsuruta et al. "Quantitation of IL-1β mRNA by a combined method of RT-PCT and an ELISA based on ion-sensitive field effect transistor" *Journal of Immunological Methods* 180:259-264 (1995).

Van Steenkist et al. "A microsensor array of biochemical sensing" *Sensors and Actuators B* 44:409-412 (1997).

* cited by examiner

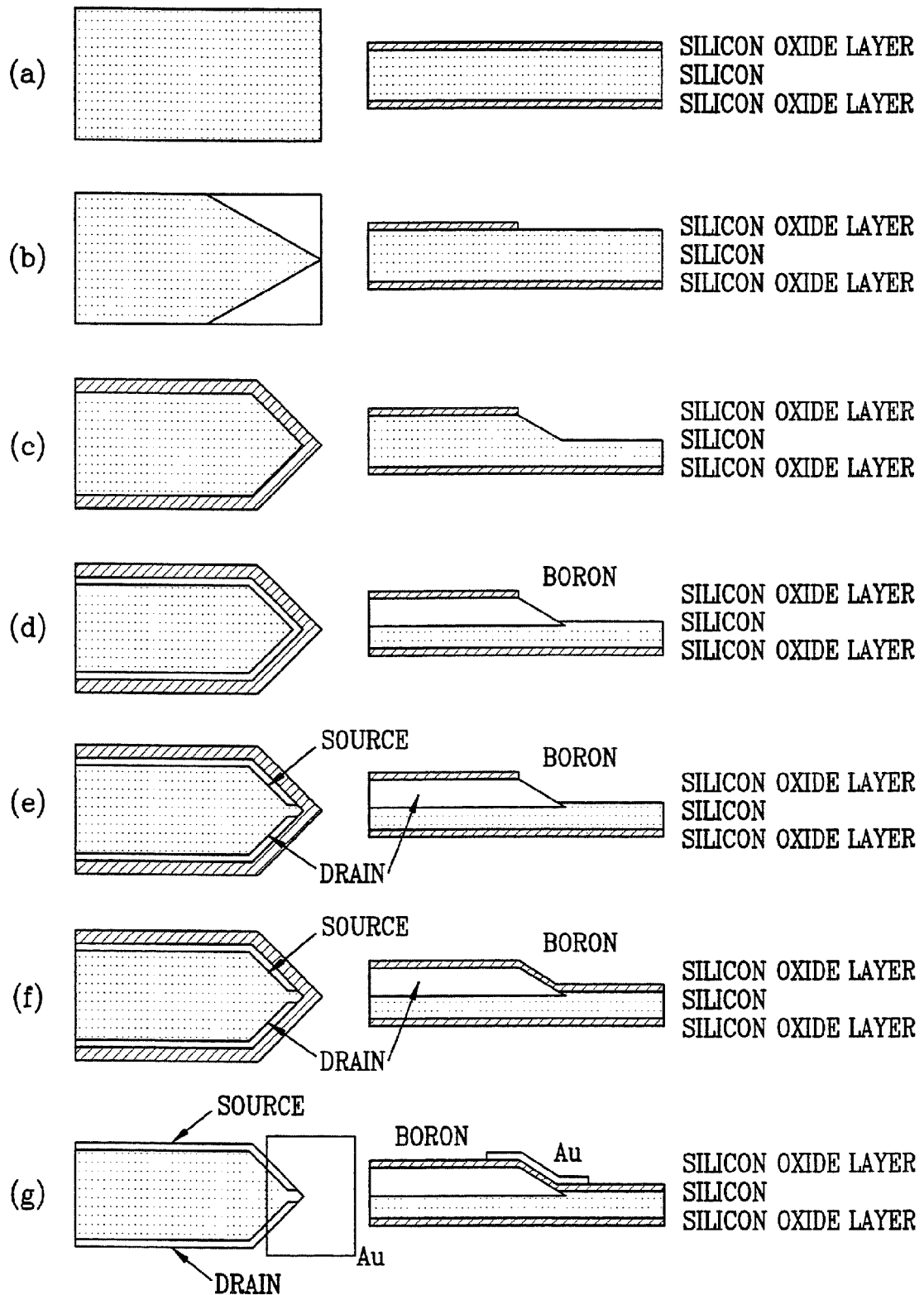

METHODS OF MAKING A MOLECULAR DETECTION CHIP HAVING A METAL OXIDE SILICON FIELD EFFECT TRANSISTOR ON SIDEWALLS OF A MICRO-FLUID CHANNEL

CROSS-REFERENCE TO RELATED APPLICATIONS

This application is a divisional of application Ser. No. 10/239,736, filed Sep. 25, 2002 now U.S. Pat. No. 7,235,389, which is a 35 U.S.C. §371 national stage application of International PCT Application No. PCT/KR02/00746 filed Apr. 23, 2002, which claims priority from Korean Application No. 2001-21752, filed Apr. 23, 2001, Korean Application No. 2001-29729 filed May 29, 2001 and Korean Application No. 2001-78010 filed Dec. 11, 2001. The disclosure and content of each of these applications are incorporated by reference herein in their entireties.

BACKGROUND OF THE INVENTION

1. Field of the Invention

The present invention relates to a molecular detection chip including a metal oxide semiconductor field effect transistor (MOSFET) formed on sidewalls of a micro-fluid channel, and a molecular detection device employing the molecular detection chip. Also, the present invention relates to a molecular detection method using the molecular detection device, and more particularly, to a quantitative detection method for the immobilization of molecular probes or the binding of molecular probes and a target sample. The present invention relates to a nucleic acid mutation assay device constructed by incorporating a thermal control and detection unit including a heater and a thermal sensor into the molecular detection device, and a nucleic acid mutation assay method using the nucleic acid mutation assay device.

2. Description of the Related Art

The disclosure of the human DNA sequence by the completion of genome project has accelerated researches into the function of diverse nucleic acids and proteins coded by the nucleic acids, and at the same time, increased the need for biosensors for easy detection of biomolecules such as nucleic acids and proteins.

Biosensors capable of sensing biomolecules using electrical signals are disclosed in U.S. Pat. Nos. 4,238,757, 4,777,019, 5,431,883, and 5,827,482. U.S. Pat. No. 4,238,757 discloses a field effect transistor (FET) designed to have a source and drain, including a layer of antibodies specific to a particular antigen. The concentration of antigens in a sample solution is measured from drain current variations over time using the FET.

U.S. Pat. No. 4,777,019 discloses a FET in which a gate is formed across doped source and drain regions, and a nucleotide complementary to a target nucleotide to be measured is bound to the top of the gate.

U.S. Pat. No. 5,431,883 discloses a FET in which a thin film of phthalocyanin, an organic insulating material capable of being changed to be conductive through reactions with chemical species, is formed to connect a gate and a drain.

U.S. Pat. No. 5,827,482 discloses a biosensor including two FETs connected in parallel, each having respective gates to which molecular receptors sensitive to different materials are bound for improved sensitivities.

However, currently available biosensors are all formed as conventional planar surface FETs each having a source, a drain, and a channel layer on the surface of a planar substrate so that high integration of the biosensors is restricted. In addition, it is difficult to selectively immobilize biomolecular probes on a limited region. Accordingly, immobilization of probes on the FETs is performed by using a separate fabrication apparatus in the fabrication of the FETs. However, the resulting probes are weakly immobilized on the FETs so that binding to a target molecule cannot be detected with high sensitivity. In addition, a considerable time is required to check for the probe immobilization, thereby increasing the overall time consumption for target molecule detection.

Therefore, there is an increasing need for a new biosensor which is easy to highly integrate, ensures stable immobilization of probes and in-situ confirmation of the probe immobilization, and can detect binding of a target molecule with high sensitivity.

Biochips refer to chips having highly immobilized biomolecular probes, such as DNA, proteins, etc., to be analyzed on substrates and are used for the analysis of a gene expression profile, genetic defects, a protein profile, and reaction patterns. Biochips can be categorized into a microarray chip having immobilized probes on a solid substrate and a lab-on-a-chip having immobilized probes on a micro-channel according to the type of immobilization of the probes, and into a DNA chip, a protein chip, etc., according to the kinds of probes.

Most DNA chips currently available are manufactured based on a spotting or photolithography technique. A DNA chip is manufactured by immobilizing only a single DNA strand that can react with a target DNA, as a probe on a particular substrate using chemical bonds, and detects the target DNA from the reaction. In manufacturing such a DNA chip, immobilization of probe DNAs greatly affects the reliability and reproducibility of products, and thus it needs to be accurately controlled. However, techniques in current use fail to accurately quantify the immobilized biomolecules.

Conventional spotting chips or photolithography chips can adjust the quantity of probes to a certain level on a volume basis in the manufacturing process, but have poor accuracy and reproducibility for use as commercial products for the diagnosis of diseases. In particular, for the investigation of particular DNA expression, more accurate immobilization of probe DNAs is required. Despite the need for an accurate immobilization technique, one has not been established yet due to technical problems in manufacturing processes and cost concerns.

To overcome the conventional problems, the present inventors have conducted research and completed the present invention where the voltage and current characteristics of a DNA chip were measured using a MOSFET sensor in the DNA chip so that immobilization and hybridization of probe DNAs could be accurately detected. As a result, a DNA chip capable of measuring the immobilization and hybridization of probe DNAs at the same time can be manufactured for commercial uses without an increase in the manufacturing cost.

Single nucleotide polymorphism (SNP) of nucleic acids, which is a single base pair variation of human DNA between individuals, is the most common DNA sequence polymorphism (about 1 per 1000 bases). SNP affects the immune system of individuals and thus can be effective for diagnosing, treating, and preventing inherited diseases. Therefore, there is a need for a rapid and convenient detection method of SNP originating from individual or racial genetic differences and immunities.

Common SNP detection methods are based on temperature-dependent separation of double-stranded DNA. Double-stranded DNA is separated into two single strands at a temperature greater than about 95° C. Based upon these characteristics, the sequence of mutated DNA can be identified. However, this method needs discrete systems and apparatuses for each step and cannot be applied for real-time DNA separation and immediate detection through accurate and precise temperature control.

U.S. Pat. No. 6,171,850 entitled "Integrated Devices and Systems for performing Temperature Controlled Reactions and Analyses" discloses use of a heat exchanger in controlling the internal and external temperatures of individual reactors. The reaction system includes a heater and at least one heat exchanger. This reaction system is merely focused on temperature control of a plurality of reactors. Also, the inclusion of the heat exchanger is not advantageous in DNA detection and improvement of fluid channel characteristics.

U.S. Pat. No. 6,174,676 entitled "Electrical Current for Controlling Fluid Parameters in Micro-channels" discloses a variety of heaters and a fluid channel equipped with an electrically controlled heater and cooler. This patent is restricted to the temperature control apparatus for PCR without description of a device for detecting temperature-based separation of DNA duplex.

U.S. Pat. No. 5,683,657 entitled "DNA meltometer" discloses a nucleic acid analytical device including a temperature control chamber for carrying a buffer solution while being kept at a predetermined temperature, a heating and cooling unit for controlling the temperature of the temperature control chamber, and a labeling and detecting unit for labeling thermally denatured double-stranded DNA at a temperature $T_m$ with fluorescent materials and detecting them. In the DNA meltometer, the DNA detecting unit is separated from the temperature control chamber, thereby complicating the overall system and causing a delay in the detection step.

To address these problems, the present inventors have developed a DNA mutation (SNP) assay device which ensures DNA detection as well as temperature adjustment in a variety of ways based upon the fact that a double-stranded DNA is separated into two single strands at an increased temperature. According to the present invention, whether DNA is separated or not can be identified in real time using a DNA detection unit disposed on a fluid channel.

SUMMARY OF THE INVENTION

It is a first object of the present invention to provide a molecular detection chip that is easy to highly integrate and can detect the immobilization of probes and binding of a target molecule in situ within a short period of time.

It is a second object of the present invention to provide a method for fabricating the molecular detection chip.

It is a third object of the present invention to provide a molecular detection device employing the molecular detection chip.

It is a fourth object of the present invention to provide a quantitative detection method of the immobilization of molecular probes using the molecular detection device.

It is a fifth object of the present invention to provide a quantitative detection method of the binding of molecular probes and a target sample using the molecular detection device.

It is a sixth object of the present invention to provide a new nucleic acid mutation assay device in which at least one thermal control and detection unit is formed in a micro-fluid channel by microfabrication so that DNA mutations can be detected in real time through accurate and precise temperature control.

It is a seventh object of the present invention to provide an effective nucleic acid mutation (single nucleotide polymorphism; SNP) assay method using the nucleic acid mutation assay device.

To achieve the first object of the present invention, there is provided a molecular detection chip comprising: a semiconductor substrate; a micro-fluid channel serving as a flow path of a molecular sample and formed in the semiconductor substrate, and a metal oxide silicon field-effect transistor (MOSFET) on sidewalls of the micro-fluid channel.

In the present invention, the term "sidewalls" of the micro-fluid channel is intended to include convex corners and bottoms as well as the actual sidewalls of the micro-fluid channel.

It is preferable that a gate electrode of the MOSFET is formed of a thin gold (Au) layer. It is preferable that thiol-substituted probes are immobilized as self-assembled monolayers on the surface of the gate electrode.

To achieve the second object of the present invention, there is provided a method for fabricating a molecular detection chip, the method comprising forming an oxide layer on the surface of a semiconductor substrate. Next, a micro-fluid channel having at least one convex corner is formed by etching the surface of the semiconductor substrate, and the sidewalls of the micro-fluid channel are doped with impurity ions to form an impurity diffusion region. A channel region of a MOSFET is defined by etching a portion of the impurity diffusion region formed on the sidewalls of the micro-fluid channel using an etching solution. An oxide layer is formed on the channel region, and a gate electrode is formed on the channel region using gold (Au), thereby resulting in a molecular detection chip according to the present invention.

It is preferable that defining the channel region is performed by selectively etching the impurity diffusion region along the at least one convex corner. In defining the channel region, it is preferable that an etch stop point is determined by measuring current level variations with application of reverse bias voltage to the semiconductor substrate.

To achieve the third object of the present invention, there is provided a molecular detection device comprising: a substrate; a molecular-sample loading unit formed on the surface of the substrate; at least one micro-fluid channel having one end connected to the molecular-sample loading unit and serving as a flow path for a molecular sample; and a MOSFET sensor connected to the other end of the micro-fluid channel and on which a molecular probe is immobilized.

Preferably, the MOSFET sensor is implemented with a molecular detection chip according to the present invention. In this case, it is preferable that the molecular detection chip is manufactured separately from a molecular detection kit including the substrate, the molecular sample loading unit, and the micro-fluid channel, and then mounted on a chip mount region located at the end of the micro-fluid channel of the molecular detection kit.

The present invention also provides a molecular sample detection method comprising providing molecular probes through a molecular-sample loading unit formed on the surface of the substrate of a molecular detection device. Next, the molecular probes are immobilized on the surface of a gate electrode of a MOSFET formed on sidewalls of a micro-fluid channel of the molecular detection device, the micro-fluid channel having one end connected to the molecular-sample loading unit and the other end connected to the MOSFET so that the molecular probes provided through the sample loading unit move through the micro-fluid channel into the MOSFET. Following this, current-voltage characteristics of the gate electrode are measured. After providing a target molecular sample through the molecular-sample loading unit, the target molecular sample is reacted with the molecular probes while moving through the fluid channel of the molecular detection device. Finally, current-voltage characteristics of the gate electrode are measured to detect the target molecular sample based on the change in the current-voltage characteristics with respect to the result measured before loading the target molecular sample.

It is preferable that the molecular detection method further comprises removing the molecular probes that are not immobilized on the gate electrode by loading a cleaning solution into the molecular-sample loading unit after immobilizing the molecular probes on the surface of the gate electrode, and removing the target sample that is not reacted with the molecular probes by loading a cleaning solution into the molecular-sample loading unit after reacting the target molecular sample with the molecular probes.

In the present invention, the molecular probes or the target molecular sample may comprise nucleic acids, proteins, enzyme substrates, adjuvants, and oligosaccharides. Preferably, the nucleic acids comprise single-stranded deoxyribonucleic acids (DNAs), single-stranded ribonucleic acids (RNAs), and single-stranded peptide nucleic acids (PNAs). Preferably, the proteins comprise agonists to cell membrane receptors, antagonists to cell membrane receptors, toxins, virus epitopes, hormones, peptides, enzymes, and monoclonal antibodies. More preferably, the molecular probes are single-stranded nucleic acids, and the target molecular sample is single-stranded nucleic acids capable of being hybridized with the molecular probes.

The molecular detection chip and device according to the preset invention are advantageously easy to highly integrate and can detect immobilization of probes and coupling of a target molecule to the probes in situ.

To achieve the fourth object of the present invention, there is provided a quantification method of the immobilization of molecular probes, the method comprising: providing the molecular probes into the molecular-sample loading unit of the molecular detection device described above; immobilizing the molecular probes on the surface of a gate electrode of the MOSFET sensor by allowing the molecular probes to move along the micro-fluid channel; and measuring current-voltage characteristics of the gate electrode.

To achieve the fifth object of the present invention, there is provided a quantification method of the binding of molecular probes and a target molecular sample, the method comprising: (a) providing the molecular probes into the molecular-sample loading unit of the molecular detection device described above; (b) immobilizing the molecular probes on the surface of a gate electrode of the MOSFET sensor by allowing the molecular probes to move along the micro-fluid channel; (c) measuring current-voltage characteristics of the gate electrode; (d) providing the target molecular sample into the molecular-sample loading unit; (e) binding the target molecular sample to the molecular probes immobilized on the surface of the gate electrode of the MOSFET sensor by allowing the target molecular sample to move along the micro-fluid channel; and (f) measuring current-voltage characteristics of the gate electrode and comparing the result of the measurement with the current-voltage characteristics measured in step (c).

According to the present invention, by measuring the current-voltage characteristics of the gate electrode of a MOSFET sensor installed in the molecular detection device, immobilization of probes and hybridization of a target sample to the immobilized probes can be quantitatively measured. For a DNA chip, immobilization of probe nucleic acids, such as single-stranded deoxyribonucleic acids (DNAs), single-stranded ribonucleic acids (RNAs), and single-stranded peptide nucleic acids (PNAs), and hybridization of target nucleic acids to the probe nucleic acids can be quantitatively measured.

To achieve the sixth object of the present invention, a heater, a thermal sensor, and a DNA sensor formed as a MOSFET sensor are built as an assembly in a micro-fluid channel for temperature-based DNA separation and detection. According to the present invention, the temperature, which affects DNA structure, is adjusted using the heater and the thermal sensor, and at the same time, whether the DNA is single- or double-stranded can be detected in real time.

In particular, the present invention provides a nucleic acid mutation assay device comprising: a substrate; a sample loading unit formed on the surface of the substrate; a micro-fluid channel directly connected to the sample loading unit to serve as a sample flow path; and at least one thermal control and detection unit formed in the micro-fluid channel and including a MOSFET sensor for nucleic acid immobilization, a heater, and a thermal sensor.

It is preferable that the heater and the thermal sensor are located adjacent to the MOSFET sensor and control a temperature which is significant to the nucleic acid immobilized on the MOSFET sensor, and the MOSFET sensor detects denaturated or renaturated double-stranded nucleic acid at the melting point $T_m$ of the immobilized nucleic acid.

In the present invention, a MOSFET is used as a sensor for detecting a charge variation before and after separation of double-stranded nucleic acid.

It is preferable that the MOSFET is located at the sidewalls or convex corners of the micro-fluid channel. Unlike recently disclosed FET-based biomolecular sensors manufactured on a plain, a biomolecular sensor according to the present invention is formed as a 3-dimensional (3D) MOSFET sensor by bulk micromachining and diffusion and is disposed at the convex corners of the micro-fluid channel. The biomolecular sensor having this structure is located in the flow path of nucleic acid, thereby reducing the area occupied by a detection unit including the sensor as well as sharply shortening detection time. Thus, more sensors can advantageously be mounted within a small space.

According to the present invention, the MOSFET used as a DNA sensor is characterized by including a thin gold (Au) layer in source and drain regions on which self-aligned monolayers of thiol-substituted nucleic acids are immobilized. In particular, the MOSFET sensor has two source and drain sensors, each coated with a thin oxide layer and in turn with an Au layer, thereby resulting in a MOS structure. Thiol groups having a selective affinity to the Au layer are attached to the ends of the nucleic acid molecule so that the thiol-substituted nucleic acid molecules are adsorbed to the Au layer. Thiol-substituted nucleic acid molecules are adsorbed to the surface of the Au layer as self-assembled monolayers (SAMs). SAMs mean organic monolayers which are spontaneously arranged on the surface of a substrate in a regular pattern and form chemical bonds with the substrate. Thus, an additional manufacturing device is not required to form SAMs. Currently available biomolecular sensors fail to provide a limited binding site to biomolecules and have a weak binding force. However, selective adsorption, which is employed in the present invention, of thiol-substituted biomolecules to Au in the form of SAMs can eliminate the drawbacks of the existing biomolecular sensors. In addition, the direct adsorption of thiol-substituted biomolecules to the surface of the sensor provides excellent performance of detecting charge variations before and after reaction.

Also, the present invention is characterized in that nucleic acids immobilized on the MOSFET sensor include single-stranded DNA, single-stranded RNA, and single-stranded peptide nucleic acid (PNA). Single-stranded nucleic acids serve as probes that are hybridized to a target nucleic acid injected through a sample loading unit. It is preferable that discrete nucleic acid sequences are immobilized on each MOSFET sensor.

In the present invention, the heater acts to raise the temperature of the thermal control and detection unit, and the thermal sensor acts to control the operation of the heater. It is preferable that the heater and the thermal sensor are located close to the MOSFET sensor for effective control of the temperature which greatly affects nucleic acids adsorbed to the MOSFET sensor.

To achieve the seventh object of the present invention, there is provided a method for assaying nucleic acid mutation, the method comprising: immobilizing single-stranded nucleic acid probes on the surface of a gate electrode of a MOSFET sensor; injecting a target nucleic acid responsive to the immobilized single-stranded nucleic acid probes into a sample loading unit and moving the target nucleic acid to the MOSFET sensor along a micro-fluid channel; hybridizing the target nucleic acid to the single-stranded nucleic acid probes immobilized on the MOSFET sensor; gradually raising a temperature to separate the double-stranded nucleic acid which are hybridized, into two single strands; and measuring current-voltage characteristics of the gate electrode of the MOSFET sensor.

In the nucleic acid mutation assay method according to the present invention, low-temperature nucleic acid hybridization is followed by gradual temperature rise to detect nucleic acid mutations. The thermal control and detection unit disposed in the micro-fluid channel enables real-time nucleic acid mutation detection through accurate and precise temperature adjustment.

Alternatively, the present invention provides a method for assaying nucleic acid mutation, the method comprising: immobilizing single-stranded nucleic acid probes on the surface of a gate electrode of a MOSFET sensor; injecting a target nucleic acid responsive to the immobilized single-stranded nucleic acid probes into a sample loading unit and moving the target nucleic acid to the MOSFET sensor along a micro-fluid channel; keeping a temperature at which hybridization of the target nucleic acid to the single-stranded nucleic acid probes does not occur; gradually dropping the temperature to renaturate single-stranded nucleic acids into double-stranded nucleic acids which are hybridized; and measuring current-voltage characteristics of the gate electrode of the MOSFET sensor. In this case, high-temperature nucleic acid denaturation is followed by gradual temperature drop to detect nucleic acid mutations.

The nucleic acid mutation assay device and method according to the present invention are effective in detecting nucleic acid mutations, particularly, single nucleotide polymorphism (SNP). Double-stranded DNA is denatured into two single-strands at a temperature of 96° C. or greater. The temperature of denaturation is relatively higher for hybrids having a perfectly matched base pair and relatively lower for hybrids having mismatched base pair. Based on this, a miniature system of thermal control and detection in which reaction temperatures can be adjusted is manufactured by micro-electro mechanical system (MEMS) techniques. If discrete nucleic acid sequences are immobilized on each DNA sensor implemented as a MOSFET sensor in the system according to the present invention, SNP of nucleic acid can be assessed by sensing the temperature at which nucleic acid denaturation occurs, using corresponding temperature control units.

BRIEF DESCRIPTION OF THE DRAWINGS

The above objects and advantages of the present invention will become more apparent by describing in detail preferred embodiments thereof with reference to the attached drawings in which:

FIG. 15 shows fabrication of a MOSFET used in the thermal control and detection unit of the nucleic acid mutation assay device according to the present invention;

DETAILED DESCRIPTION OF THE INVENTION

Figure 1:
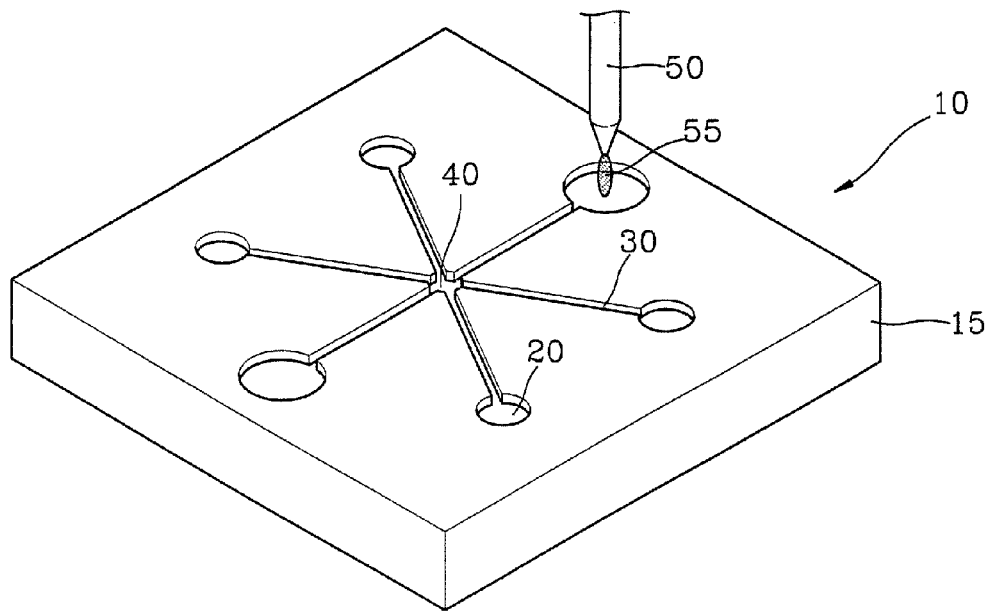
FIG. 1 is a perspective view of a preferred embodiment of a molecular detection device according to the present invention.

A molecular detection chip, a molecular detection device employing the molecular detection chip, a method for fabricating the molecular detection chip, and a molecular detection method using the molecular detection device according to the present invention now will be described more fully with reference to the accompanying drawings. This invention may, however, be embodied in many different forms and should not be construed as being limited to the embodiments set forth herein; rather, these embodiments are provided as that this disclosure will be thorough and complete, and will fully convey the concept of the invention to whose skilled in the art.

In the drawings, the thickness of layers are exaggerated for clarity, and like reference numerals are used to refer to like elements throughout.

FIG. 1 is a perspective view of a preferred embodiment of the molecular detection device according to the present invention. Referring to FIG. 1, the molecular detection device includes a molecular detection kit 10 and a molecular detection chip (not shown) mounted on the molecular detection kit 10. The molecular detection kit 10 includes at least one sample loading unit 20 formed in the surface of a substrate 15, which is connected to a chip mount region 40 through a fluid channel 30. The width and depth of the fluid channel 30 are determined to be large enough to allow a sample to flow by capillary action. In FIG. 1, reference numeral 50 denotes a sample dispenser, and reference numeral 55 denotes a molecular sample.

Although not illustrated in FIG. 1, the molecular detection kit 10 includes a variety of electric devices that can communicate with the molecular detection chip mounted on the chip mount region 40 through electric signals.

In the embodiment of FIG. 1, the molecular detection chip is described as being detached from the molecular detection kit 10, but it may also be attached to the same for measurement. Alternatively, the molecular detection chip may be built into the molecular detection kit 10 if necessary.

Figure 2:
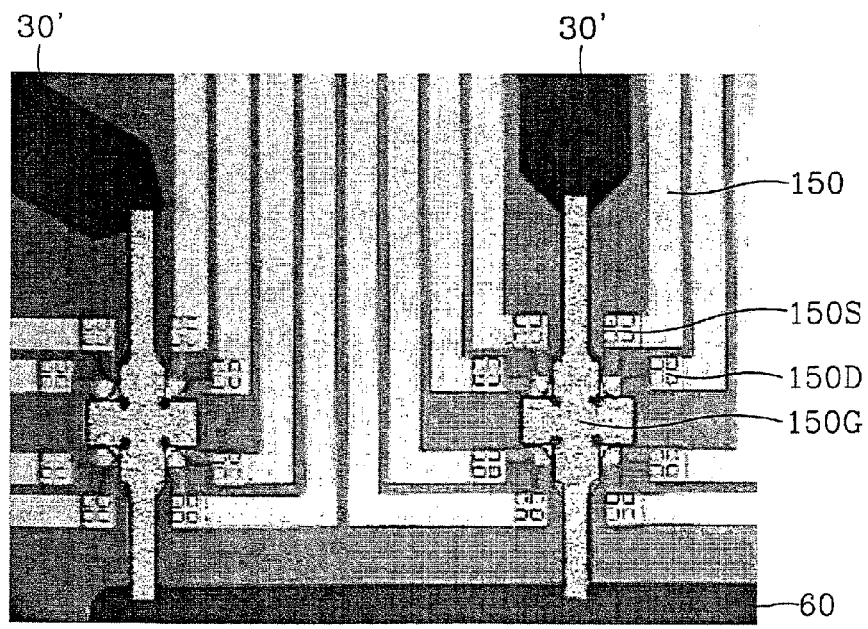
FIG. 2 is a partial top view of molecular detection chips according to a preferred embodiment of the present invention.

FIG. 2 is a partial top view of molecular detection chips according to a preferred embodiment of the present invention to be mounted in the chip mount region 40 of the molecular detection kit 10 of FIG. 1. Referring to FIG. 2, each molecular detection chip includes a micro-fluid channel 30' connected to one end of the fluid channel 30 having the other end connected to a corresponding sample loading unit 20 of the molecular detection kit 10 of FIG. 1, and a sample exhaust unit 60 connected to the opposite end of the micro-fluid channel 30'. Source electrodes 150S, drain electrodes 150D, and gate electrodes 150G are formed on the surface of the molecular detection chip, and interconnects 150 are connected to the source electrodes 150S or drain electrodes 150D.

The structure of the molecular detection chip according to the preferred embodiment of the present invention shown in FIG. 2 will be described in greater detail with reference to FIG. 3, which is a partial perspective view of one molecular detection chip of FIG. 2.

Figure 3:
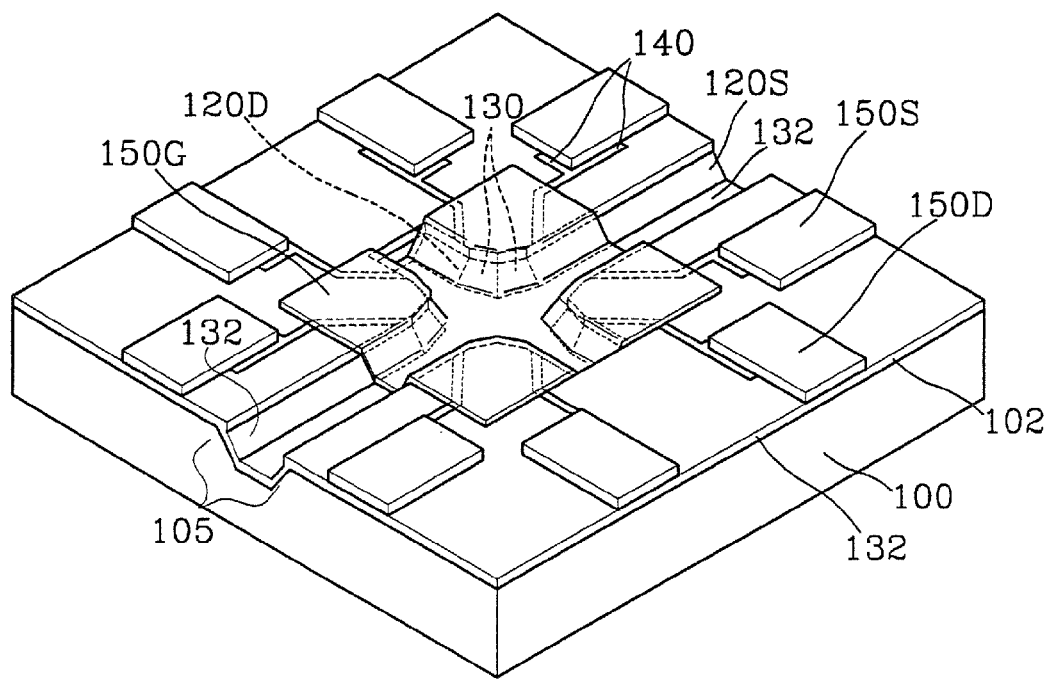
FIG. 3 is a partial perspective view of one molecular detection chip (metal oxide semiconductor field-effect transistor (MOSFET) sensor) of FIG. 2.

Referring to FIG. 3, a micro-fluid channel 105 as a sample flow path is formed on the surface of a semiconductor substrate 100. Four metal oxide silicon field-effect transistors (MOSFETs) are formed on the sidewalls of the micro-fluid channel 105. The molecular detection chip according to the present invention can include at least one MOSFET. Each of the MOSFETs includes source and drain regions 120S and 120D formed on the sidewalls of the micro-fluid channel 105 by doping impurity ions, and a channel region 130 defined on the convex corners of the micro-fluid channel 105 by the source and drain regions 120S and 120D. A gate electrode 150G is formed in each channel region 130 with a gate insulating layer 132 interposed therebetween. The gate electrode 150G is preferably formed of a thin gold (Au) layer such that probes, to which a target molecule is coupled, are stably immobilized as self-assembled monolayers. Interconnects 140 for connecting the source and drain regions 120S and 120D to source and drain electrodes 150S and 150D, respectively, are formed on the surface of the substrate 100.

Figure 4:
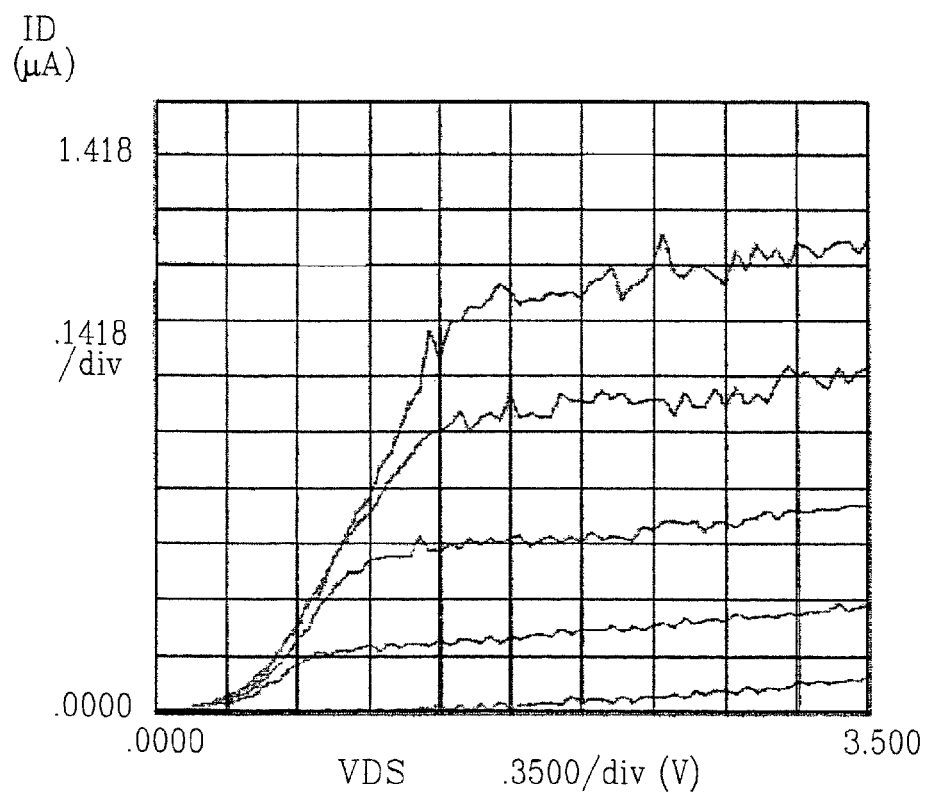
FIG. 4 is a graph of the current-voltage (I-V) characteristics of the molecular detection chip of FIG. 2.

A current-voltage (I-V) characteristic curve for the molecular detection chip of FIG. 3 is shown in FIG. 4. As shown in FIG. 4, the preferred embodiment of the molecular detection chip according to the present invention shows normal electrical characteristics for a MOSFET.

Figure 5:
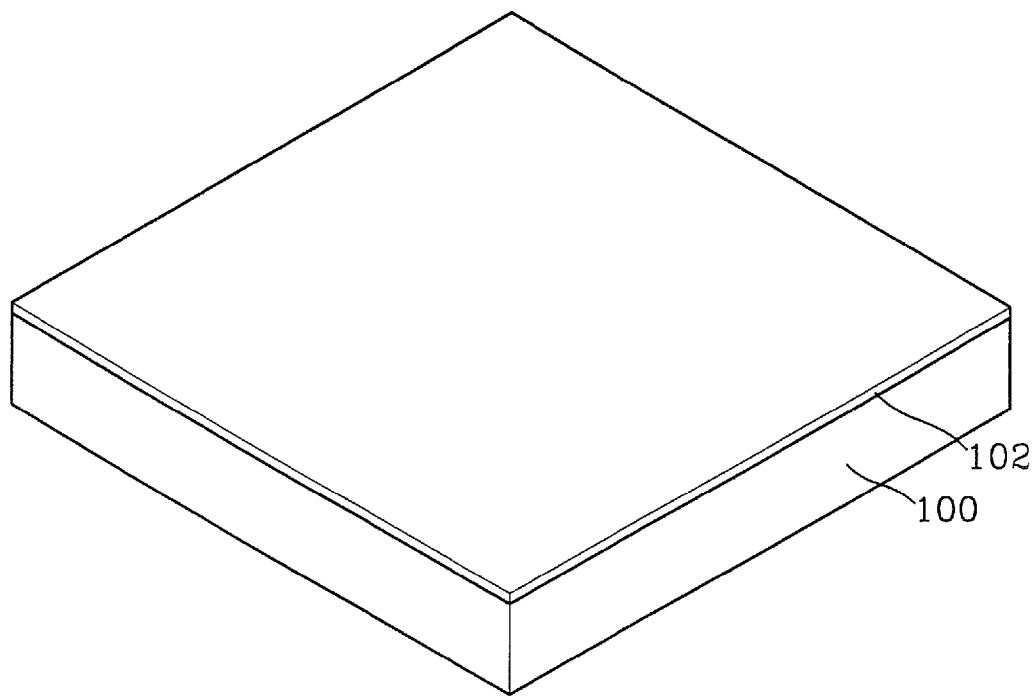
FIGS. 5 through 9 are perspective views illustrating each step of a method for fabricating a molecular detection chip according to a preferred embodiment of the present invention.

A method for fabricating the molecular detection chip of FIG. 3 will be described with reference to FIGS. 5 through 9. Referring to FIG. 5, a silicon oxide layer 102 is formed on a semiconductor substrate 100 to a thickness of 1.5-2.0 µm. It is preferable that the semiconductor substrate 100 is an n-type silicon substrate with a (100) direction plane.

Figure 6:
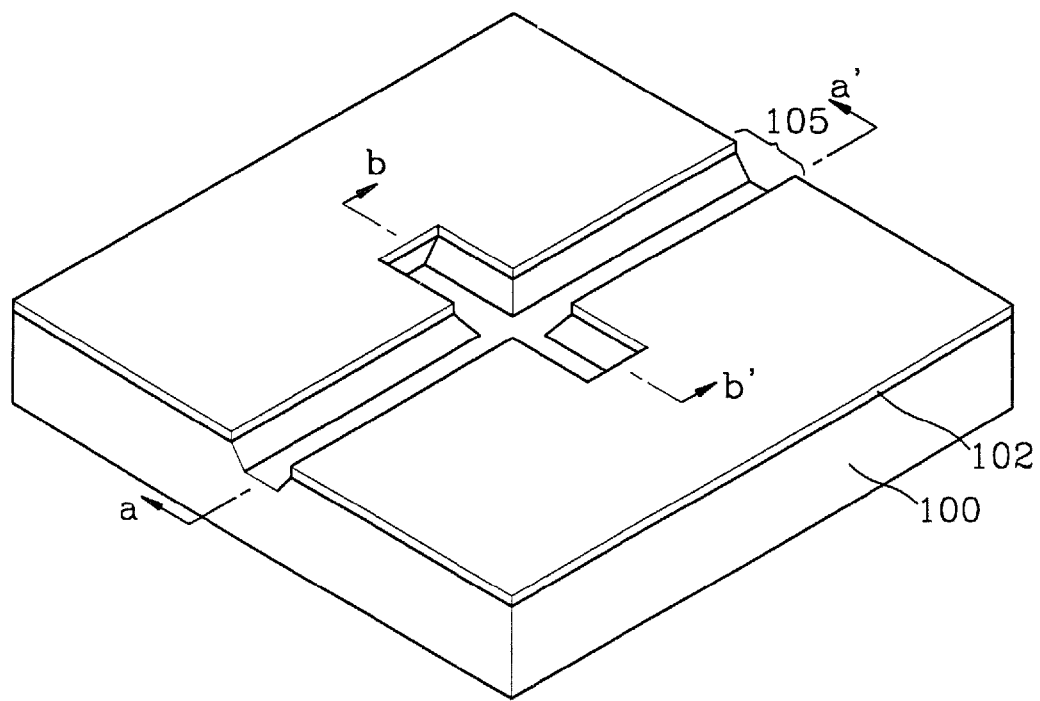

Next, as shown in FIG. 6, a micro-fluid channel 105 having at least one convex corner is formed in the semiconductor substrate 100 by photolithography. The reason for the need of at least one convex corner will be described in a subsequent process. In the present embodiment of FIG. 6, although the micro-fluid channel 105 is formed to be longer in the direction of line a-a' and relatively shorter, but long enough to form at least one convex corner, in the direction of line b-b', it will be appreciated that the micro-fluid channel 105 may be stretched in the direction of line b-b' to form bidirectional, crossed micro-fluid channels if needed.

Figure 7A:
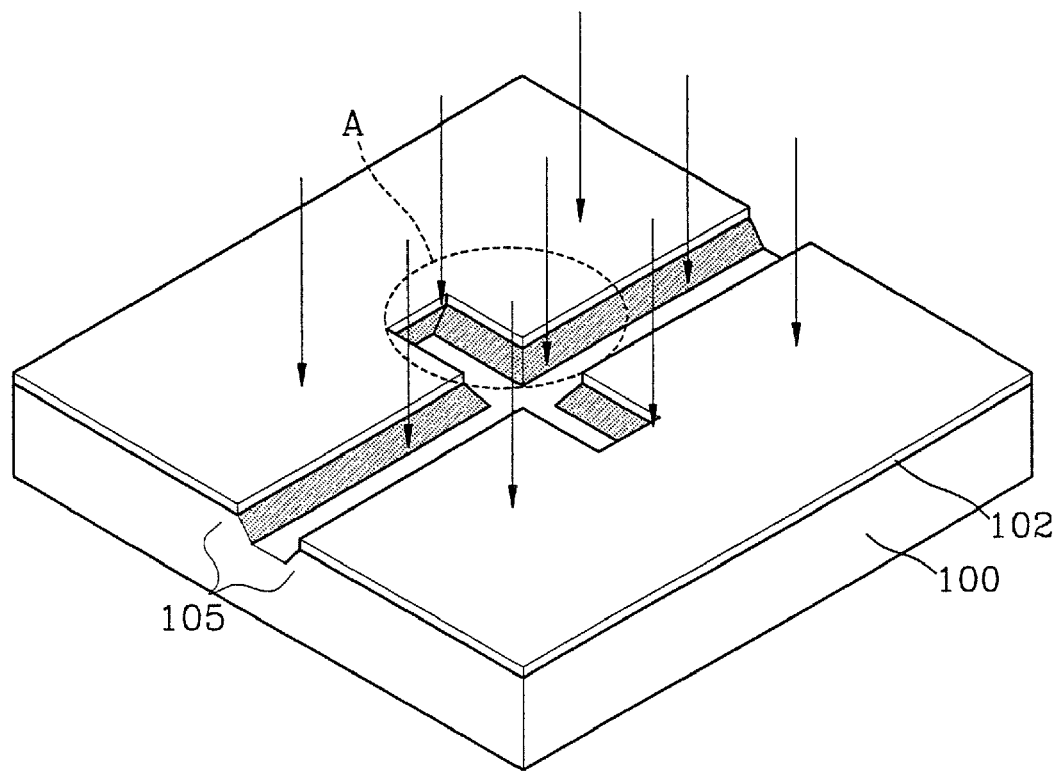

Next, as shown in FIG. 7A, the entire surface of the substrate 100 is doped with impurity ions. P-type impurity ions are used for the doping of the substrate 100. For example, the substrate 100 may be doped with boron at a concentration of $10^{16}$-$10^{18}$ atoms/cm$^2$. Based on oxide removal rate with respect to the thickness of a natural silicon oxide layer, by controlling implantation conditions, such as temperature and time, only the sidewalls of the micro-fluid channel 105, not the bottom, can be doped with impurity ions. Through a subsequent diffusion process, an impurity diffusion region 110 is formed only on the sidewalls of the micro-fluid channel 105, as shown in FIG. 7B, which is a partial enlarged view of FIG. 7A.

Figure 7B:
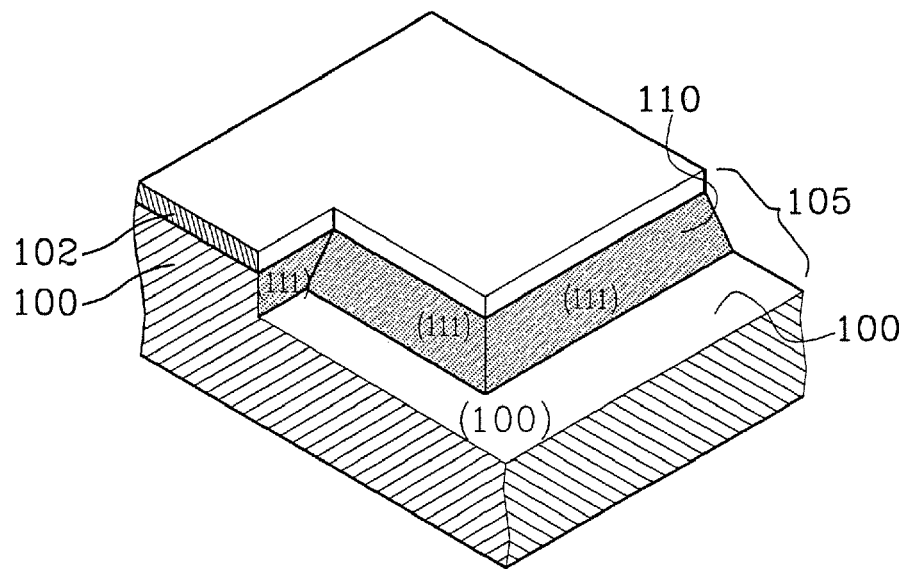
Figure 8A:
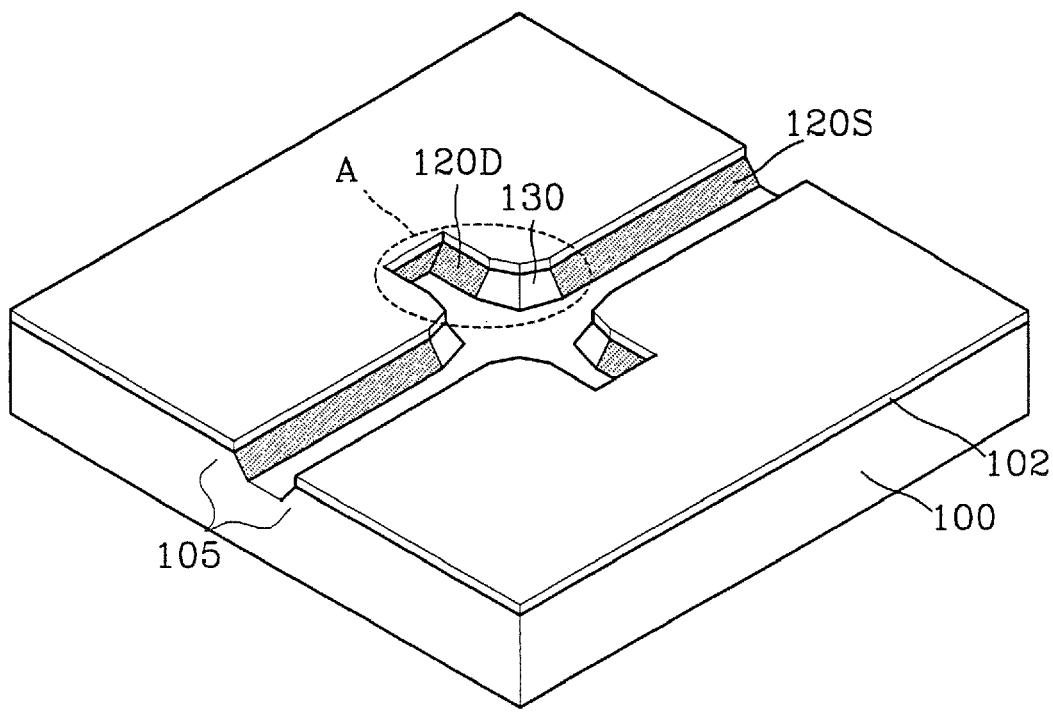

The resultant structure of FIG. 7B is etched using an etching solution. A trimethylammonium hydroxide (TMAH) solution is preferably used as the etching solution. Since only the convex corners of the micro-fluid channel 105 are selectively etched, the impurity diffusion region 110 is partially opened, resulting in an open region serving as a channel region 130 at the corners of the micro-fluid channel 105, as shown in FIG. 8A. As a result, a source region 120S, a drain region 120D, and the channel region 130 are formed.

Figure 8B:
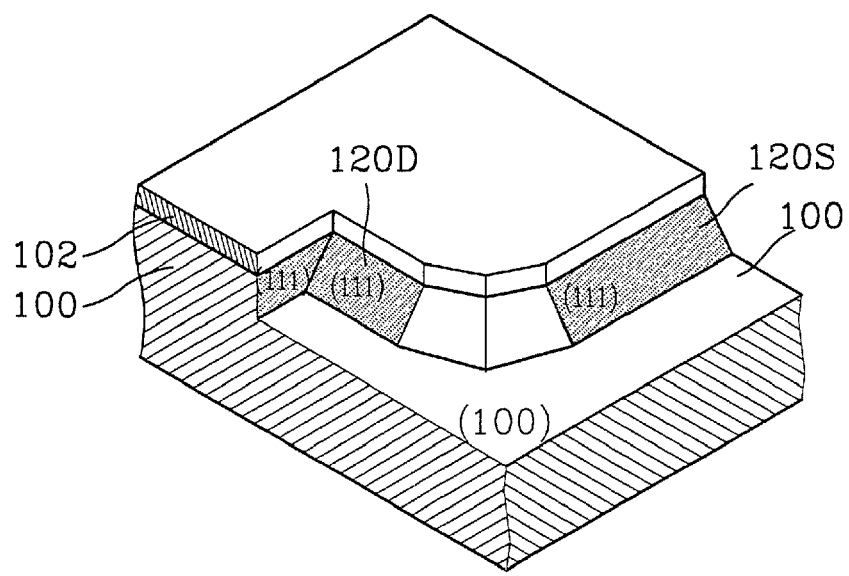

The reason for selective etching on the convex corners of the micro-fluid channel 105 lies in the fact that crystal orientation direction differs from one region to another region that is made contact with the etching solution, as shown in FIG. 8B. The bottom surface of the micro-fluid channel 105 is formed by the (100) direction plane, like the original silicon substrate 100, whereas the etched sidewalls of the micro-fluid channel 105 are comprised of a (111) direction plane. Therefore, the convex corners of the micro-fluid channels 105, at which the (111) direction planes meet, are selectively etched at a predetermined angle.

Whether the impurity diffusion region 110 is opened to form the channel region 130 can be easily detected by etching the substrate 100 with an application of reverse bias voltage. When the impurity diffusion region 110 is shorted, current does not flow although a reverse bias voltage is applied to the impurity diffusion region 110. However, current starts to flow as soon as the impurity diffusion region 110 is opened at the corners of the micro-fluid channel 105 by etching. An etch stop point is easily determined based on current variations.

Figure 9:
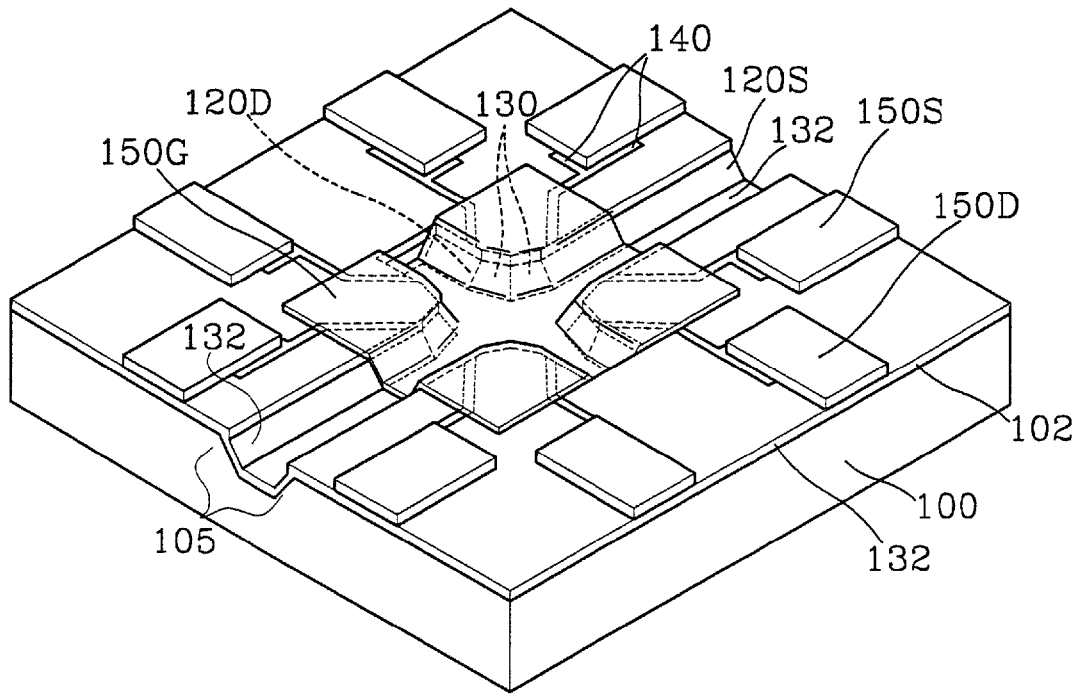

Lastly, a gate insulation layer 132 is formed on the substrate 100 in which the source region 120S, the drain region 120D, and the channel region 130 are formed, as shown in FIG. 9, and a gate electrode 150G is formed. The gate insulation layer 132 is formed of a silicon oxide layer to have a thickness of 300-800 Å. The gate electrode 150G is formed as a thin gold (Au) layer to enable easy immobilization of high-density probes thereon. It is preferable that a thin chromium (Cr) layer is formed prior to the formation of the thin Au layer to improve adhesion of the gate electrode 150G made of Au to the gate insulation layer 132. Interconnects 140 connected to the source regions 120S or drain regions 120D, and source and drain electrodes 150S and 150D are formed through general processes, thereby forming a molecular detection chip.

Figure 10:
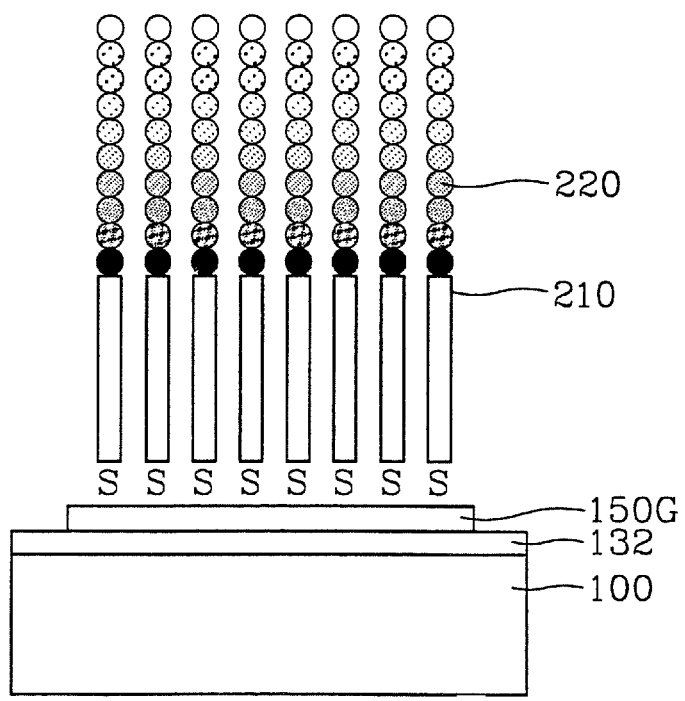
FIG. 10 is a view illustrating immobilization of probes on a gate electrode of the molecular detection chip.

A molecular detection method using the molecular detection device according to the present invention now will be described with reference to FIGS. 1 and 3. Initially, the surface of the molecular detection chip is cleaned with a piranha solution (a mixture of $H_2SO_4$ and $S_2O$ in a ratio of 3:1) and then with deionized water, followed by drying using nitrogen gas and treating with UV ozone. As a result, organic substance is removed from the surface of the chip. The surface of the molecular detection kit 10 is cleaned in the same manner as the surface of the chip. After the cleaning step is finished, the molecular detection chip of FIG. 3 is mounted on the chip mount region 40 of the molecular detection kit 10 of FIG. 1. Next, a probe sample is applied into the sample loading unit 20 of FIG. 1. A probe sample having a thiol group at its end is used. The probe sample moves along the fluid channels 30 of FIG. 1 connected to the sample loading unit 20 by capillary action. The probe sample is immobilized on the top of the gate electrode 150G of each MOSFET formed on the sidewalls of the micro-fluid channel 105 of FIG. 3 in the form of self-assembled monolayers while passing along the micro-fluid channel 105 connected to each of the fluid channels 30. Sample probes being immobilized on the surface of the gate electrode 150 are shown in FIG. 10. When probes are immobilized as self-assembled monolayers on the top of the gate electrode 150G formed of Au, thiol groups serving as linkers are used. In FIG. 10, reference numeral 210 denotes thiol groups, and reference numeral 220 denotes probes. Such selective immobilization of self-assembled monolayers of probes on the gate electrode 150G made of Au using the thiol groups 210 as linkers results in a highly dense and well-aligned structure of the immobilized probes with strong binding force, as shown in FIG. 10. As a result, stable coupling with a target molecule can be maintained through a subsequent reaction process.

Suitable probes may include nucleic acids, proteins, enzyme substrates, adjuvants, and oligosaccharides, which are responsive to a target molecule. Single-stranded deoxyribonucleic acid (DNA), single-stranded ribonucleic acid (RNA), or single-stranded peptide nucleic acid (PNA) can be used as a nucleic acid. Suitable proteins include agonists to cell membrane receptors, antagonists to cell membrane receptors, toxins, virus epitopes, hormones, peptides, enzymes, and monoclonal antibodies.

After the probe immobilization on the gate electrode 150G, voltage and current flowing across the gate electrode 150G are measured.

Next, a target sample is applied into the sample loading unit 20 of FIG. 1. The target sample refers to biomolecular samples from live organisms and synthetic samples. The target sample moves along the fluid channel 30 connected to the sampling loading unit 20 and finally passes through the micro-fluid channel 105 of FIG. 3 of the molecular detection chip connected to the fluid channel 30. The target sample reacts with the probes 220 of FIG. 10 while passing through the micro-fluid channel 105.

Current-Voltage (I-V) characteristics on the gate electrode 150G are measured, and whether or not the target sample is coupled to the probes is determined by measuring the change in I-V characteristics before and after the sample-to-probe binding.

For another sample detection, the probes used are removed from the gate electrode 150G made of Au. The probes used can be removed by washing the gate electrode 150G using the piranha solution (a 3:1 mixture of $H_2SO_4$ and $S_2O$).

Next, the same processes described above are repeated for the new target sample using probes that are responsive to the target sample to detect the target sample.

According to the present invention, the immobilization of probes on the gate electrode 150G as self-assembled monolayers is easy to perform with excellent reproducibility. Separation of the probes for another sample detection is also easy. Thus, the molecular detection device according to the present invention is advantageous in that a variety of probes can easily be used.

Figure 11:
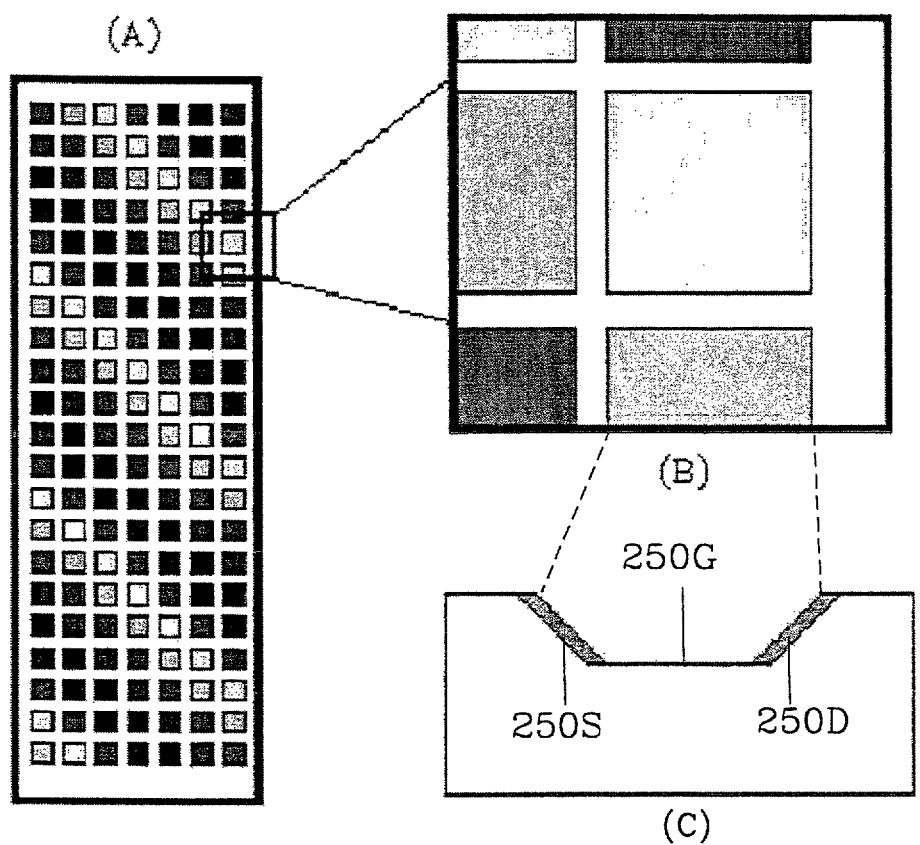
FIG. 11 is a view of a preferred embodiment of a detection apparatus of probe DNAs immobilized using a spotting or photolithography technique according to the present invention.

According to the present invention, a MOSFET sensor can be formed on the sidewalls of a micro-fluid channel, as shown in FIG. 3, or can be underneath the surface of a general planar biochip. FIG. 11 shows a detection system for measuring the quantity of DNAs immobilized on a DNA chip using the MOSFET sensor installed underneath the DNA chip surface. In FIG. 11, (A) shows the DNA chip manufactured using a spotting or photolithography technique, (B) shows an enlarged region of one spot, and (C) shows a structure of the MOSFET sensor including a source region 250S, a drain region 250D, and a gold (Au)-film deposited gate region 250G.

Figure 12:
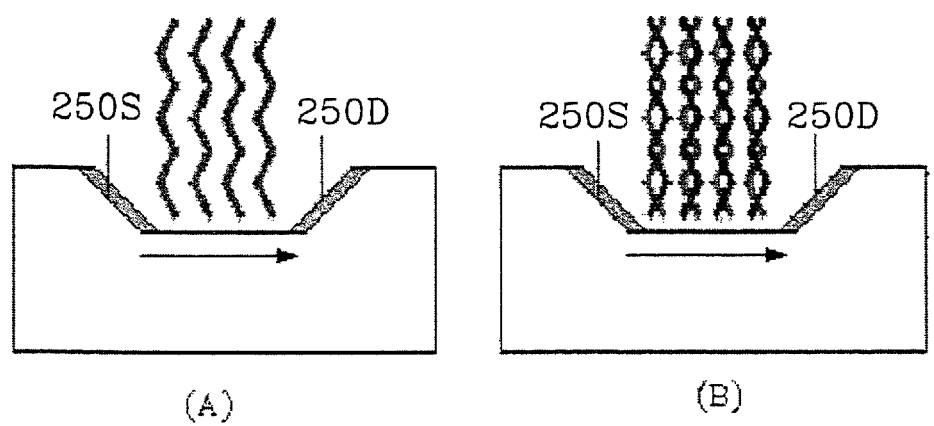
FIG. 12 is a view of a preferred embodiment of a detection method of the hybridization of probe DNAs and a target DNA according to the present invention.

FIG. 12 shows a detection system for quantifying the immobilization of prove DNAs and target DNAs in each spot region. In FIG. 12, (A) shows only single-stranded probe DNAs immobilized on the Au region of a DNA chip (i.e., the surface of a MOSFET sensor), and (B) shows the probe DNAs being hybridized to the target DNAs.

In manufacturing a spotting chip or photolithography chip, glass is generally used for a substrate. In the present invention, a silicon wafer is preferred for the substrate. Silicon wafers have electrical characteristics as well as excellent mechanical properties, compared to glass, and thus can be applied for DNA immobilization and detection systems with excellent characteristics. By attaching a thiol-substituted group to the end of probe DNAs, the probe DNAs can be selectively immobilized only on the Au region patterned in a silicon wafer.

Figure 13:
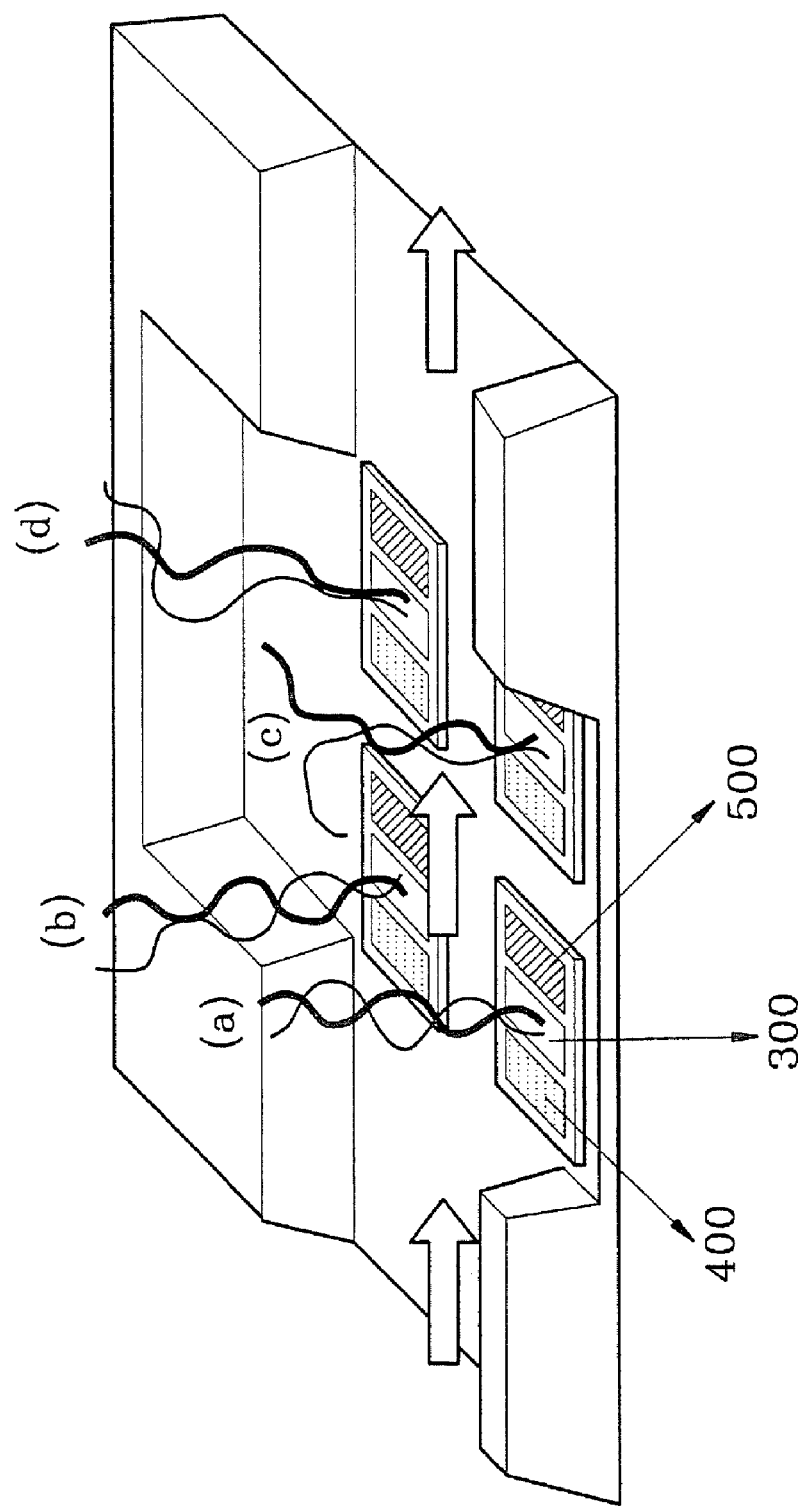
FIG. 13 is a diagram of a preferred embodiment of a nucleic acid mutation assay device according to the present invention in which thermal control and detection units are disposed on the bottom of a micro-fluid channel.

FIG. 13 shows a preferred embodiment of a nucleic acid mutation assay device according to the present invention, in which a plurality of thermal control and detection units are disposed on the bottom of a micro-fluid channel, wherein each thermal control detection unit includes a MOSFET sensor 300, a heater 400, and a thermal sensor 500. In FIG. 13, the arrows indicate the direction in which fluid flows, and strands extending from the MOSFET sensor 300 are DNA strands. In particular, (a) indicates perfectly matched DNA hybrids, and (b), (c), and (d) indicate mismatched DNA hybrids.

Figure 14:
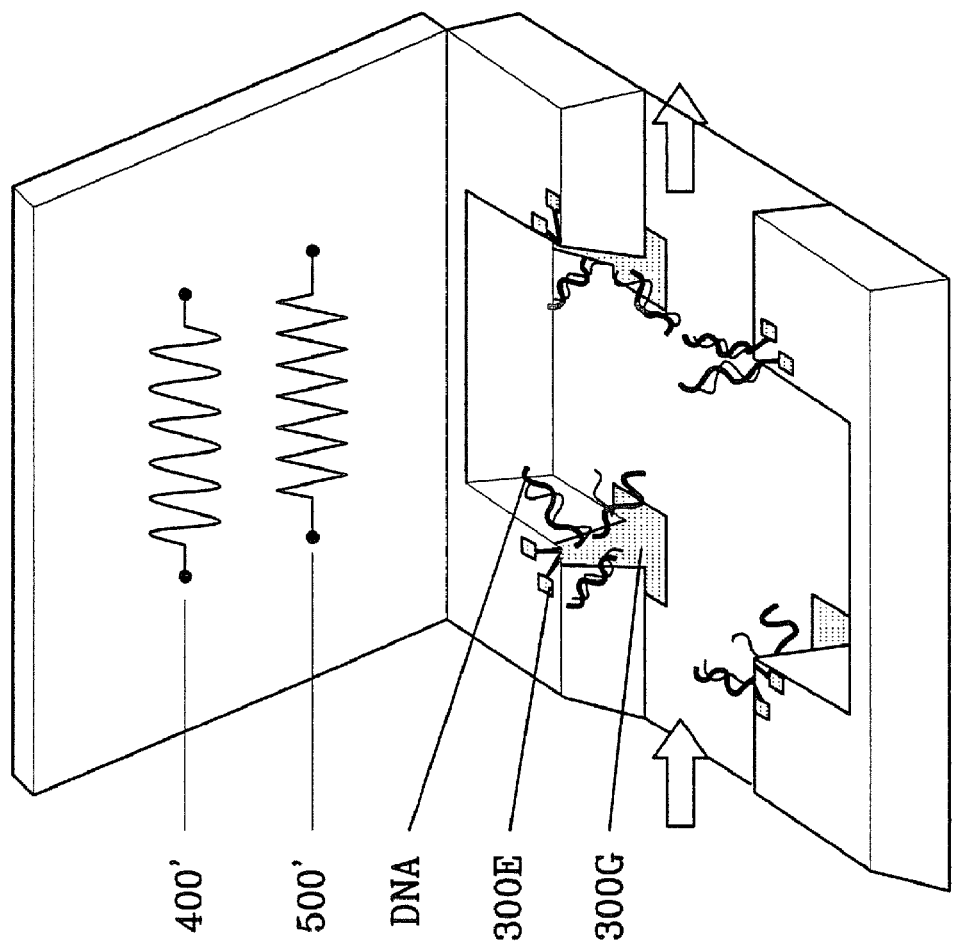
FIG. 14 is a diagram of another preferred embodiment of the nucleic acid mutation assay device according to the present invention, in which MOSFETs of a thermal control and detection unit, on which nucleic acids are immobilized, are formed on the sidewalls or convex corners of a micro-fluid channel, and a thermal control and detection unit having a heater and a thermal sensor is disposed above the micro-fluid channel.
Figure 16A:
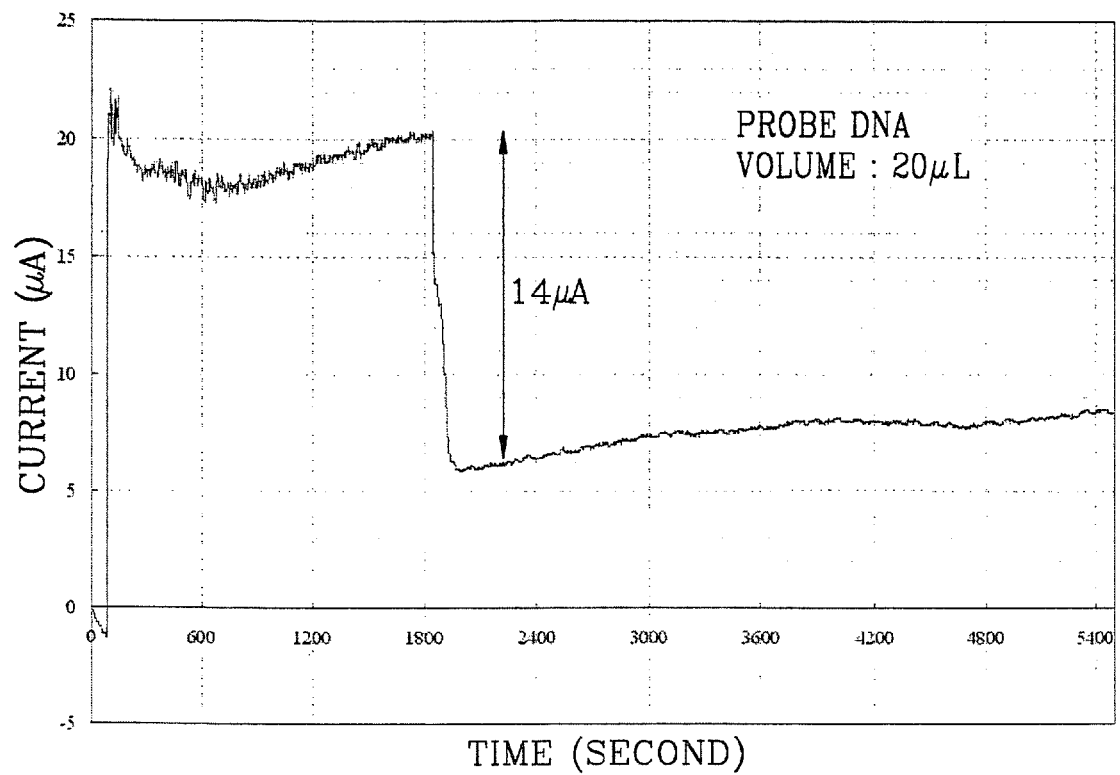
FIG. 16 is a graph of the current variation with respect to the amount of probe DNAs immobilized on a biochip according to the present invention.
Figure 16B:
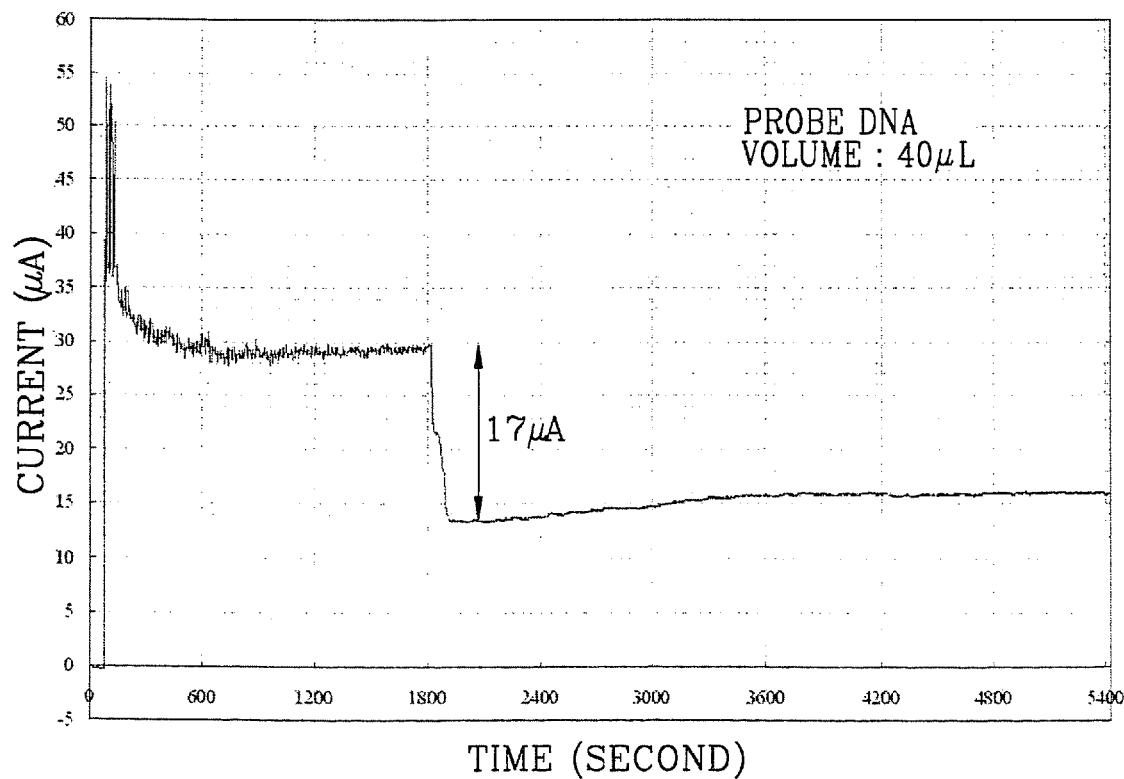
Figure 16C:
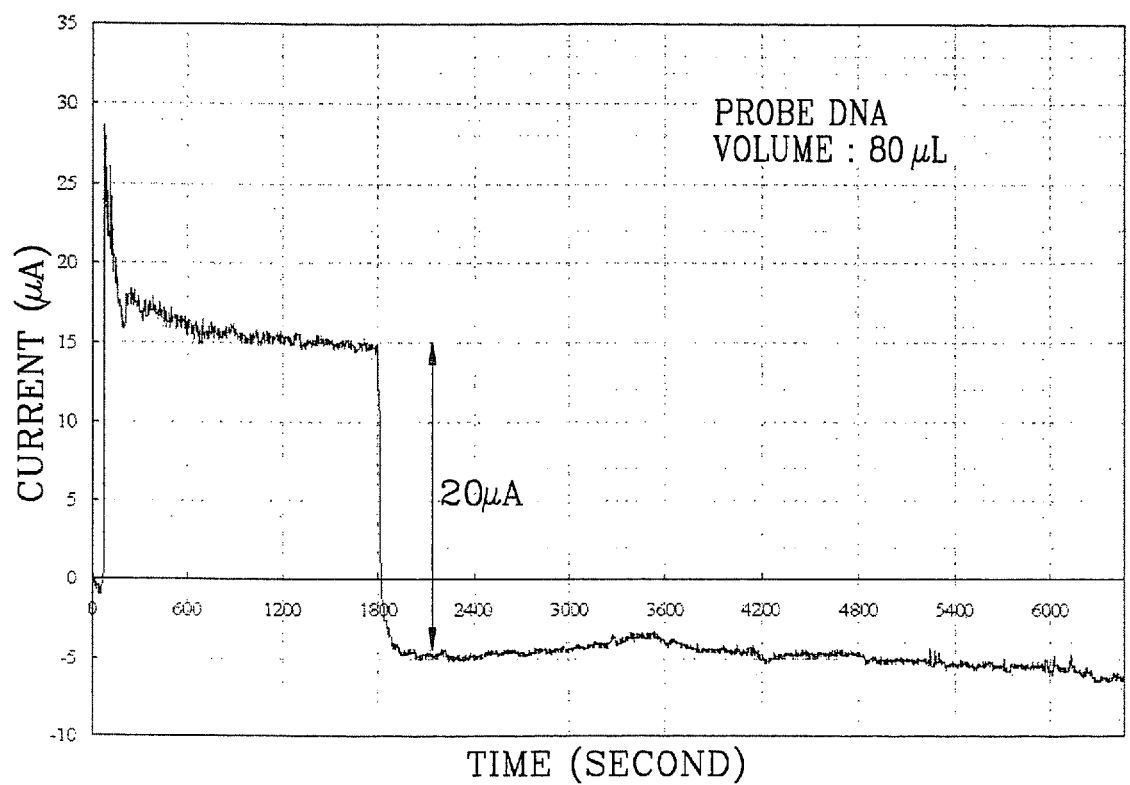
Figure 16D:
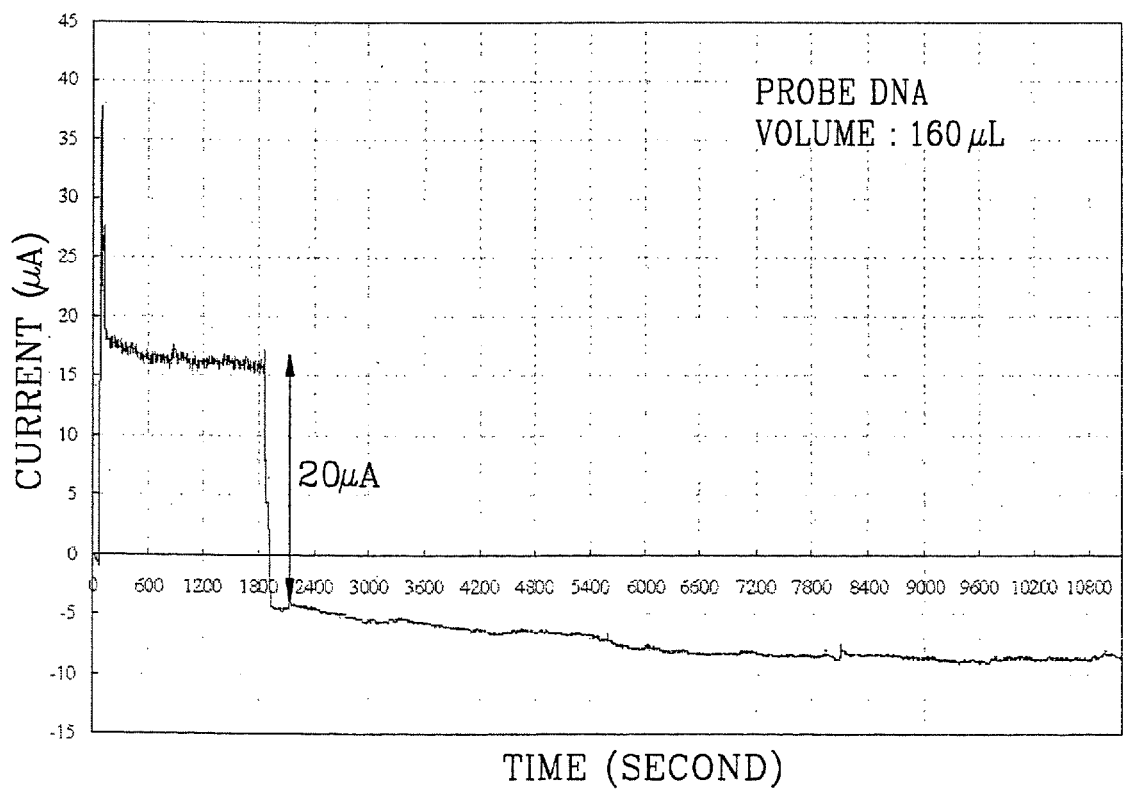

FIG. 14 shows another preferred embodiment of the nucleic acid mutation assay device according to the present invention, in which MOSFET sensors of the thermal control and detection unit, each having an electrode 300E and a Au gate 300G, are disposed on the sidewalls or convex corners of the micro-fluid channel, and a micro-heater 400' and micro-thermal sensor 500' are mounted above the micro-fluid channel.

The present invention will be described in greater detail with reference to the following embodiments. The following embodiments are for illustrative purposes and are not intended to limit the scope of the invention.

Embodiment 1

Fabrication of Molecular Detection Device or Nucleic Acid Mutation Assay Device 1. Formation of Micro-fluid Channel In general, the body of the molecular detection device or the nucleic acid mutation assay device according to the present invention can be assembled using a method and material compatible with microfabrication techniques. For example, the body of the molecular detection device or the nucleic acid mutation assay device may include a polymer-based part formed by injection molding using a variety of polymers, or a plurality of planar crystalline substrates formed of silicon, glass, etc. A variety of wells or channels may be formed in a crystalline substrate made of, for example, silica, glass or silicon, by etching, milling, drilling, etc. These materials and methods are compatible with microfabrication techniques that are widely used in semiconductor related industries. Available microfabrication techniques include, for example, electrodeposition, low-pressure vapor deposition, photolithography, etching, laser drilling, etc.

Photolithography is more compatible to etch substrates in the microfabrication of the nucleic acid mutation assay device according to the present invention. For example, a substrate is overlaid with a photoresist and exposed through a photolithographic mask to electromagnetic rays to form a photoresist pattern, which reflects chambers and/or channels to be formed in the molecular detection device or the assay device. The exposed substrate is etched to form desired wells or channels. Next, the substrate on which the wells and/or channels are formed is covered and bonded with another planar substrate. Suitable photoresists include polymethyl methacrylate (PMMA) and its derivatives, electron beam resists such as poly(olefin sulfones) and the like.

Preferably, the body of the molecular detection device or the nucleic acid mutation assay device may be formed by combining a part formed by injection molding using, for example, plastic, and a planar silica or silicon substrate that is etched. For example, a sample loading unit may be formed by injection molding, whereas the micro-fluid channel or well, a thermal control and detection unit may be formed in a planar glass, silica, or silicon chip or substrate by etching in microfabrication.

2. Formation of DNA Detection Unit (Sensor)

FIG. 15 shows fabrication of a DNA detection unit (MOSFET sensor) to be mounted at convex corners of the micro-fluid channel. A nucleic acid injected into a sample loading unit moves to a detection site of the sensor along the micro-fluid channel. First, an n-type silicon substrate is wet etched and followed by boron diffusion to form a p-type silicon region on the etched sidewalls. The boron-doped region is divided into source and drain regions by wet etching. To form a MOSFET structure, a thin oxide layer is formed on the source and drain regions, and chromium (Cr) is deposited on the oxide layer for improved adhesion to Au. Next, Au is deposited on the Cr layer. Thiol-substituted nucleic acid probes are immobilized on the surface of the sensor. Thiol-substituted nucleic acids are selectively bound as self-assembled monolayers (SAMs) to only the Au layer on the surface of the sensor. The DNA detection unit for the molecular detection device or the nucleic acid mutation assay device according to the present invention is fabricated by forming a thin Au layer on a DNA sensor of MOSFET and then immobilizing thiol-substituted nucleic acids on the Au layer. SAMs of thiol-substituted nucleic acid attached to the Au layer are easily formed with excellent reproducibility. In addition, the variable opposite ends of the thiol groups have wide applications. SAMs of the thiol-substituted nucleic acids are denser and are better assembled than other SAMs and are stable in a variety of reactions following the formation of SAMs due to a strong binding force.

3. Formation of Thermal Control Unit

A thermal control unit is formed by including a heater and a thermal sensor to control the temperature of a DNA detection unit (formed as a MOSFET sensor) which affects the structure of nucleic acid attached to the same.

A thin-film resistive heater, which is known in the art, may be used as the heater. The heater can be formed by depositing a metallic thin film below, above, or inside the micro-fluid channel to be connected to a power source. As the thermal sensor, a bimetal thermocouple for generating temperature-dependent electromotive force (EMF), a resistive thermometer or thermistor including temperature-dependent electric resistance material, an IC thermal sensor, a quartz thermometer, etc. may be used.

Embodiment 2

Quantification of Probe DNA Immobilization

For quantification of the immobilization of probe DNAs, the chip of FIG. 3 was mounted on the chip mount region 40 of the molecular detection kit 10 of FIG. 1, and a voltage was applied. Synthetic DNA probes (5-thiol-GTTCTTCTCAT-CATC-3') having substituted thiol groups at 5'-terminal were loaded into the sample loading unit 20 in different volumes 20 µL, 40 µL, 80 µL, and 160 µL, respectively, and current variations over time were measured.

The results are shown in FIG. 16. As shown in FIG. 16, as the quantity of probe DNAs loaded into the sensor increases, the current dropping level flowing across the drain and source of the sensor proportionally increases. As a result, the current dropping level was 14 µA for 20 µL of the probe DNA (FIG. 16A), 17 µA for 40 µL of the probe DNA (FIG. 16B), and 20 µA for 80 µL of the probe DNA (FIG. 16C). No increase in current dropping level was observed for more than 80 µL of the probe DNA (FIG. 16D).

Accordingly, by measuring the current level flowing across the gate electrode of the sensor, probe DNAs immobilized on a DNA chip can be quantitatively measured. The quantification of the probe DNAs provides basic data on reactions with a target DNA in the DNA chip.

Embodiment 3

Quantification of Probe DNA and Target DNA Hybridization

For quantification of the hybridization of probe DNAs to a target DNA, a voltage was applied to the lab-on-a-chip of FIG. 3, and synthetic DNA probes (5'-thiol-GTTCTTCT-CATCATC-3') having substituted thiol groups at 5'-terminal and a target DNA having a complementary sequence to the synthetic DNA probe were sequentially loaded. Then, current variations over time were measured.

The chip of FIG. 3 was mounted on the chip mount region 40 of the molecular detection kit 10 of FIG. 1, and current flowing through the chip was measured with the application of a voltage. Next, a phosphate buffer solution was injected into the sample loading unit 20 of the molecular detection kit 10. Current measurement continued as the phosphate buffer solution was injected. Immediately after the buffer injection, the current level increased, as shown by reference A of FIG.

Figure 17:
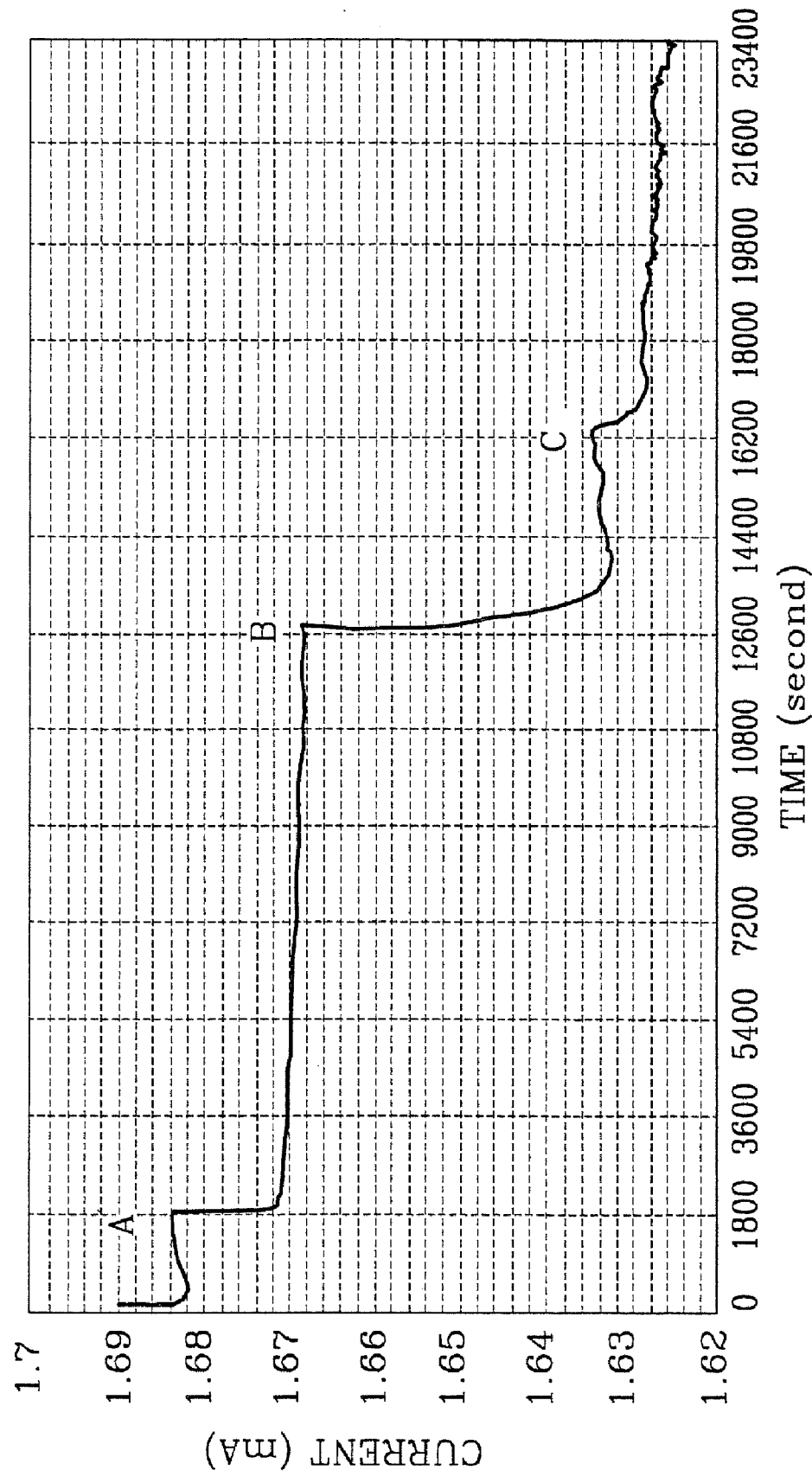
FIG. 17 is a graph of the current variation as a probe DNA and target DNA are hybridized together according to the present invention.

17. Next, the current level stabilized for about 30 minutes. Then probes of 15 basepair (bp) synthetic DNA (5'-thiol-GTTCTTCTCATCATC-3') having substituted thiol groups at 5'-terminal were loaded into the sample loading unit 20. After the probe DNA was loaded, the current level dropped, as shown by reference B of FIG. 17. This indicates that the probe DNA has been immobilized as self-assembled monolayers on the surface of the gate electrode 150G made of Au of FIG. 3. Thus, immobilization of probe DNA can be detected in situ. Observation of current variations continued until a sufficient current drop was detected, i.e., for about 3 hours, and then deionized water was loaded into the same loading unit 20 to get rid of free non-immobilized probe DNA and the phosphate buffer solution. Next, tris-EDTA buffer was supplied through the sample loading unit 20 and left for about 1 hour while monitoring current level variations to provide optimal hybridization conditions for probe and target DNAs. After the current level dropped to a level corresponding to reference C of FIG. 17, a target DNA, which is complementary to the probe DNA, was loaded into the sample loading unit 20, followed by a current level measurement. As shown in FIG. 17, after loading of the target DNA into the chip, a drop of current level of the chip occurred. Thus, hybridization between target and probe DNAs can be detected in situ.

The molecular detection chip according to the present invention is designed to have MOSFETs on the sidewalls of a micro-fluid channel so that it is possible to highly integrate the molecular detection chip with increased detection sensitivity. In addition, immobilization of probes directly on the surface of a gate electrode in the form of self-assembled monolayers ensures the molecular detection chip to check for the immobilization of probes and coupling of a target molecule to the probes in situ. The immobilization of probes as self-assembled monolayers provides a dense and stable coupling structure with high reproducibility. The immobilized probes can easily be separated for another sample detection. The molecular detection device provides reliable detection results and can detect a variety of target molecules by selectively using appropriate probes.

According to the present invention, the probes immobilized on the biochip can be quantitatively measured using MOSFET sensors built in the biochip. In addition, binding of the probes and a target sample can be quantitatively measured. For a DNA chip, immobilization of probe DNAs and hybridization to the target DNA can be accurately measured at the same time using the MOSFET sensor. Therefore, DNA chips for commercial uses can be manufactured without an increase in the manufacturing cost.

In addition, according to the present invention, a heater, a thermal sensor, and a DNA sensor are all built in the micro-fluid channel so that temperature-based nucleic acid denaturation can be detected in real time. A variety of types of nucleic acid mutations, particularly single nucleotide polymorphisms (SNPs), can be effectively detected.

A conventional method for assaying the sequence of mutated DNA needs separate equipment and machine tools for temperature-based DNA helix separation and detection. It is difficult to detect DNAs separated through accurate and precise temperature control using the conventional method. According to the present invention, thermal control and detection units are disposed in the micro-fluid channel so that DNA mutations can be detected in real time through accurate and precise temperature adjustment by merely injecting a DNA sample into the micro-fluid channel. The temperature distribution is more uniform throughout the micro-fluid channel, thereby improving reliability in assay results.

While this invention has been particularly shown and described with reference to preferred embodiments thereof, it will be understood by those skilled in the art that various changes in form and details may be made therein without departing from the spirit and scope of the invention as defined by the appended claims.

What is claimed is:

1. A method for fabricating a molecular detection chip, the method comprising:
   forming an oxide layer on the surface of a semiconductor substrate;
   forming at least one micro-fluid channel having sidewalls comprising at least one convex corner by etching the surface of the semiconductor substrate;
   forming an impurity diffusion region by doping the sidewalls of the at least one micro-fluid channel with impurity ions;
   defining a channel region of a metal oxide silicon-field effect transistor (MOSFET) formed in the convex corner and further defining a source region and a drain region spaced apart from each other and formed in the sidewalls of the convex corner by etching a portion of the impurity diffusion region formed on the sidewalls of the at least one micro-fluid channel using an etching solution;
   forming an additional oxide layer on the channel region; and
   forming a gate electrode on the channel region.

2. The method of claim 1, wherein defining the channel region is performed by selectively etching the impurity diffusion region along the at least one convex corner.

3. The method of claim 1, wherein, in defining the channel region, an etch stop point is determined by measuring current level variations with application of reverse bias voltage to the semiconductor substrate.

4. The method of claim 1, wherein the gate electrode on the channel region is formed using gold (Au).

5. A method of fabricating a molecular detection chip comprising:
   forming an oxide layer on a surface of a semiconductor substrate;
   forming at least one micro-fluid channel on the semiconductor substrate, wherein the at least one micro-fluid channel comprises sidewalls comprising at least one convex corner formed by etching the surface of the semiconductor substrate and the at least one micro-fluid channel serves as a flow path of a molecular sample on the semiconductor substrate;
   forming an impurity diffusion region by doping the sidewalls of the at least one micro-fluid channel with impurity ions;
   defining a channel region of a metal oxide silicon field-effect transistor (MOSFET), wherein the MOSFET comprises the channel region formed in the convex corner, a source region and a drain region spaced apart from each other and formed in the sidewalls of the convex corner, by etching a portion of the impurity diffusion region formed on the sidewalls of the at least one micro-fluid channel using an etching solution;
   forming an additional oxide layer on the channel region; and
   forming a gate electrode on the channel region.

6. The method of claim 5, wherein defining the channel region is performed by selectively etching the impurity diffusion region along the at least one convex corner.

7. The method of claim 5, wherein, in defining the channel region, an etch stop point is determined by measuring current level variations with application of reverse bias voltage to the semiconductor substrate.

8. The method of claim 5, wherein the gate electrode on the channel region is formed using gold (Au).

9. A method of fabricating a molecular detection device comprising:

forming a molecular-sample loading unit on the surface of a substrate;

forming at least one micro-fluid channel on the semiconductor substrate, wherein the at least one micro-fluid channel comprises sidewalls comprising at least one convex corner formed by etching the surface of the semiconductor substrate and the at least one micro-fluid channel serves as a flow path of a molecular sample on the semiconductor substrate; and forming a metal oxide silicon-field effect transistor (MOSFET) sensor connected to the other end of the micro-fluid channel and on which a molecular probe is immobilized, wherein the MOSFET comprises a channel region formed in the convex corner, a source region and a drain region spaced apart from each other and formed in the sidewalls of the convex corner and a gate electrode formed on the channel region.

10. A method of claim 1, wherein thio-substituted probes are immobilized as self-assembled monolayers on the surface of the gate electrode.

* * * * *